United States Patent
Duff et al.

(10) Patent No.: US 9,029,614 B2
(45) Date of Patent: May 12, 2015

(54) PHASING REACTOR PRODUCT FROM HYDROGENATING ACETIC ACID INTO ETHYL ACETATE FEED TO PRODUCE ETHANOL

(71) Applicant: Celanese International Corporation, Irving, TX (US)

(72) Inventors: Emily Duff, League City, NC (US); R. Jay Warner, Houston, TX (US); Heiko Weiner, Pasadena, TX (US); Radmila Wollrab, Pasadena, TX (US); Zhenhua Zhou, Houston, TX (US); James Zink, League City, TX (US); Andrew Shuff, League City, TX (US)

(73) Assignee: Celanese International Corporation, Irving, TX (US)

( * ) Notice: Subject to any disclaimer, the term of this patent is extended or adjusted under 35 U.S.C. 154(b) by 365 days.

(21) Appl. No.: 13/681,901

(22) Filed: Nov. 20, 2012

(65) Prior Publication Data

US 2013/0158302 A1 Jun. 20, 2013

Related U.S. Application Data

(60) Provisional application No. 61/570,608, filed on Dec. 14, 2011.

(51) Int. Cl.
| | | |
|---|---|---|
| C07C 29/149 | (2006.01) | |
| C07C 29/147 | (2006.01) | |
| C07C 67/00 | (2006.01) | |
| C07C 29/86 | (2006.01) | |

(52) U.S. Cl.
CPC ............. *C07C 29/147* (2013.01); *C07C 29/149* (2013.01); *C07C 67/00* (2013.01); *C07C 29/86* (2013.01)

(58) Field of Classification Search
CPC .................................................... C07C 29/149
USPC ........................................................ 568/885
See application file for complete search history.

(56) References Cited

U.S. PATENT DOCUMENTS

| | | |
|---|---|---|
| 1,469,447 A | 10/1923 | Schneible |
| 2,591,671 A | 4/1952 | Catterall |
| 2,591,672 A | 4/1952 | Catterall |
| 2,607,719 A | 8/1952 | Eliot et al. |
| 2,702,783 A | 2/1955 | Harrison et al. |
| 2,715,604 A | 8/1955 | Weaver, Jr. |
| 2,744,939 A | 5/1956 | Kennel |
| 2,801,209 A | 7/1957 | Muller et al. |
| 3,404,186 A | 10/1968 | Bailey et al. |
| 3,408,267 A | 10/1968 | Miller et al. |
| 3,445,345 A | 5/1969 | Katzen et al. |
| 3,884,981 A | 5/1975 | Kiff |
| 3,990,952 A | 11/1976 | Katzen et al. |
| 4,306,942 A | 12/1981 | Brush et al. |
| 4,395,576 A | 7/1983 | Kwantes et al. |
| 4,421,939 A | 12/1983 | Kiff et al. |
| 4,422,903 A | 12/1983 | Messick et al. |
| 4,448,644 A | 5/1984 | Foster et al. |
| 4,454,358 A | 6/1984 | Kummer et al. |
| 4,456,775 A | 6/1984 | Travers et al. |
| 4,481,146 A | 11/1984 | Leupold et al. |
| 4,497,967 A | 2/1985 | Wan |
| 4,517,391 A | 5/1985 | Schuster et al. |
| 4,541,897 A | 9/1985 | Sommer et al. |
| 4,600,571 A | 7/1986 | McCarroll et al. |
| 4,611,085 A | 9/1986 | Kitson |
| 4,628,130 A | 12/1986 | Bournonville et al. |
| 4,678,543 A | 7/1987 | Houben et al. |
| 4,761,505 A | 8/1988 | Diana et al. |
| 4,774,365 A | 9/1988 | Chen et al. |
| 4,837,368 A | 6/1989 | Gustafson et al. |
| 4,842,693 A | 6/1989 | Wheldon |
| 4,943,354 A | 7/1990 | Osterburg et al. |
| 5,004,845 A | 4/1991 | Bradley et al. |
| 5,035,776 A | 7/1991 | Knapp |
| 5,124,004 A | 6/1992 | Grethlein et al. |
| 5,149,680 A | 9/1992 | Kitson et al. |

(Continued)

FOREIGN PATENT DOCUMENTS

| | | |
|---|---|---|
| CN | 201768393 | 3/2011 |
| CN | 102091429 | 6/2011 |
| CN | 101525272 | 5/2012 |
| CN | 202214306 | 5/2012 |
| DE | 2723611 | 11/1978 |
| EP | 0137749 | 4/1985 |
| EP | 0372847 | 6/1990 |
| EP | 2060553 | 5/2009 |
| JP | 51-86391 | 7/1993 |
| JP | 2009-263356 | 11/2009 |
| JP | 2010-159212 | 7/2010 |
| WO | WO 82/03854 | 11/1982 |
| WO | WO 83/03409 | 10/1983 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/063174 | 5/2009 |
| WO | WO 2009/063176 | 5/2009 |
| WO | WO 2011/097197 | 8/2011 |
| WO | WO 2011/097227 | 8/2011 |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

(Continued)

*Primary Examiner* — Elvis O Price

(57) ABSTRACT

Disclosed herein are processes for alcohol production by reducing ethyl acetate produced by hydrogenating acetic acid in the presence of a suitable catalyst. The product of the acetic acid hydrogenation is fed directly to a decanter to separate the hydrogenation product into an aqueous phase comprising water and ethanol and an organic phase comprising ethyl acetate. The organic phase is reduced with hydrogen in the presence of a catalyst to obtain a crude reaction mixture comprising the alcohol, in particular ethanol, which may be separated from the crude reaction mixture. Thus, ethanol may be produced from acetic acid through an ethyl acetate intermediate without an esterification step. This may reduce the recycle of ethanol in the hydrogenolysis process and improve ethanol productivity.

20 Claims, 13 Drawing Sheets

(56) References Cited

U.S. PATENT DOCUMENTS

| | | |
|---|---|---|
| 5,185,481 A | 2/1993 | Muto et al. |
| 5,198,592 A | 3/1993 | Van Beijnum et al. |
| 5,215,902 A | 6/1993 | Tedder |
| 5,250,271 A | 10/1993 | Horizoe et al. |
| 5,284,983 A | 2/1994 | Muto et al. |
| 5,414,161 A | 5/1995 | Uhm et al. |
| 5,449,440 A | 9/1995 | Rescalli et al. |
| 5,488,185 A | 1/1996 | Ramachandran et al. |
| 5,565,068 A | 10/1996 | Parker et al. |
| 6,093,845 A | 7/2000 | Van Acker et al. |
| 6,462,231 B1 | 10/2002 | Yanagawa et al. |
| 6,509,180 B1 | 1/2003 | Verser et al. |
| 6,632,330 B1 | 10/2003 | Colley et al. |
| 6,693,213 B1 | 2/2004 | Kolena et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,927,048 B2 | 8/2005 | Verser et al. |
| 7,074,603 B2 | 7/2006 | Verser et al. |
| 7,351,559 B2 | 4/2008 | Verser et al. |
| 7,361,794 B2 | 4/2008 | Grosso |
| 7,507,562 B2 | 3/2009 | Verser et al. |
| 7,553,397 B1 | 6/2009 | Colley et al. |
| 7,572,353 B1 | 8/2009 | Vander et al. |
| 7,594,981 B2 | 9/2009 | Ikeda |
| 7,652,167 B2 | 1/2010 | Miller et al. |
| 7,682,812 B2 | 3/2010 | Verser et al. |
| 7,732,173 B2 | 6/2010 | Mairal et al. |
| 7,744,727 B2 | 6/2010 | Blum et al. |
| 7,790,938 B2 | 9/2010 | Kawasaki et al. |
| 7,820,852 B2 | 10/2010 | Johnston et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,947,746 B2 | 5/2011 | Daniel et al. |
| 7,964,379 B2 | 6/2011 | Verser et al. |
| 8,002,953 B2 | 8/2011 | Lee et al. |
| 8,053,610 B2 | 11/2011 | Kikuchi et al. |
| 8,062,482 B2 | 11/2011 | Warner |
| 8,080,684 B2 | 12/2011 | Hassan et al. |
| 8,088,832 B2 | 1/2012 | Melnichuk et al. |
| 8,129,436 B2 | 3/2012 | Tirtowidjojo et al. |
| 8,198,057 B2 | 6/2012 | Padgett |
| 8,288,596 B2 | 10/2012 | Garton et al. |
| 8,299,132 B2 | 10/2012 | Gracey et al. |
| 8,299,133 B2 | 10/2012 | Gracey et al. |
| 2004/0195084 A1 | 10/2004 | Hetherington et al. |
| 2007/0144886 A1 | 6/2007 | Sylvester et al. |
| 2008/0135396 A1 | 6/2008 | Blum |
| 2009/0166172 A1 | 7/2009 | Casey et al. |
| 2010/0121114 A1 | 5/2010 | Johnston et al. |
| 2010/0197486 A1 | 8/2010 | Johnston et al. |
| 2010/0197959 A1 | 8/2010 | Johnston et al. |
| 2010/0273229 A1 | 10/2010 | Verser et al. |
| 2011/0004034 A1 | 1/2011 | Daniel et al. |
| 2011/0046421 A1 | 2/2011 | Daniel et al. |
| 2011/0098501 A1 | 4/2011 | Johnston et al. |
| 2011/0224462 A1 | 9/2011 | Ditzel et al. |
| 2013/0131198 A1 | 5/2013 | Warner et al. |
| 2013/0131393 A1 | 5/2013 | Warner et al. |
| 2013/0131394 A1 | 5/2013 | Warner et al. |
| 2013/0131395 A1 | 5/2013 | Warner et al. |
| 2013/0131396 A1 | 5/2013 | Warner et al. |
| 2013/0131397 A1 | 5/2013 | Warner et al. |
| 2013/0131398 A1 | 5/2013 | Warner et al. |
| 2013/0131400 A1 | 5/2013 | Duff et al. |
| 2013/0158297 A1 | 6/2013 | Johnson et al. |

OTHER PUBLICATIONS

International Search Report and Written Opinion mailed Mar. 13, 2013 in corresponding International Application No. PCT/US2012/066080.

US 9,029,614 B2

PHASING REACTOR PRODUCT FROM HYDROGENATING ACETIC ACID INTO ETHYL ACETATE FEED TO PRODUCE ETHANOL

CROSS REFERENCE TO RELATED APPLICATIONS

This application claim priority to U.S. App. No. 61/570,608, filed Dec. 14, 2011, the entirety of which is incorporated herein by reference.

FIELD OF THE INVENTION

The present invention relates generally to alcohol production from acetic acid hydrogenation to form ethyl acetate, and in particular to producing ethanol by reducing ethyl acetate. When hydrogenating acetic acid to ethyl acetate, at least 70% of the acetic acid is converted and less than 45% of the acetic acid is converted to ethanol. The reactor product may be phase separated to form an ethyl acetate feed that is reduced to ethanol. In one embodiment, the reactor product of acetic acid hydrogenation may be fed directly to a decanter, eliminating the need for the separate removal of acetic acid or other impurities prior to phase separation.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulose materials, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds, including esters, has been widely studied, and a variety of combinations of catalysts, supports, and operating conditions have been mentioned in the literature.

More recently, even though it may not still be commercially viable it has been reported that ethanol can be produced from hydrogenating acetic acid using a cobalt catalyst at superatmospheric pressures such as about 40 to 120 bar, as described in U.S. Pat. No. 4,517,391.

On the other hand, U.S. Pat. No. 5,149,680 describes a process for the catalytic hydrogenation of carboxylic acids and their anhydrides to alcohols and/or esters utilizing a platinum group metal alloy catalyst. The catalyst is comprised of an alloy of at least one noble metal of Group VIII of the Periodic Table and at least one metal capable of alloying with the Group VIII noble metal, admixed with a component comprising at least one of the metals rhenium, tungsten or molybdenum. Although it has been claimed therein that improved selectivity to a mixture of alcohol and its ester with the unreacted carboxylic acid is achieved over the prior art references it was still reported that 3 to 9 percent of alkanes, such as methane and ethane are formed as by-products during the hydrogenation of acetic acid to ethanol under their optimal catalyst conditions.

U.S. Pat. No. 7,863,489 describes the direct and selective production of ethanol from acetic acid using a platinum/tin catalyst.

U.S. Pat. No. 7,820,852 describes the direct and selective production of ethyl acetate from acetic acid utilizing a bimetal supported catalyst.

U.S. Pub. No. 2010/0197959 describes processes for making ethyl acetate from acetic acid. Acetic acid is hydrogenated in the presence of a catalyst under conditions effective to form ethyl acetate, wherein the catalyst comprises a first metal, a second metal and a support. The first metal is selected from the group consisting of nickel, palladium, and platinum and is present in an amount greater than 1 wt. %, based on the total weight of the catalyst.

U.S. Pub. No. 2010/0197486 describes catalysts for making ethyl acetate from acetic acid. The catalyst comprises a first metal, a second metal, and a support. The first metal is selected from the group consisting of nickel, palladium and platinum, and is present in an amount greater than 1 wt. %, based on the total weight of the catalyst. The second metal may be selected from the group consisting of molybdenum, rhenium, zirconium, copper, cobalt, tin and zinc, and wherein the catalyst has a selectivity to ethyl acetate of greater than 40%.

U.S. Pub. No 2011/0098501 describes processes for making ethanol or ethyl acetate from acetic acid using bimetallic catalysts. The catalyst comprises platinum, tin, and at least one support, wherein the molar ratio of platinum to tin is from 0.4:0.6 to 0.6:0.4.

U.S. Pub. No. 2010/0121114 describes tunable catalyst gas phase hydrogenation of carboxylic acids and also describes ethanol production processes by reduction of acetic acid. The catalyst comprises platinum and tin. A gaseous stream comprising hydrogen and acetic acid in the vapor phase, with a molar ration of at least 4:1 hydrogen to acetic acid, at a temperature between 225 and 300° C. is passed over a hydrogenation catalyst comprising platinum and tin dispersed on a silicaceous support. The amounts and oxidation states of the platinum and tin, as well as the ratio of platinum to tin, and the silicaceous support are selected, composed and controlled such that at least 80% of the acetic acid is converted to ethanol, less than 4% of the acetic acid is converted to compounds other than compounds selected from the group consisting of ethanol, acetaldehyde, ethyl acetate, ethylene and mixtures thereof, and the activity of the catalyst declines by less than 10% when exposed to a vaporous mixture of acetic acid and hydrogen at a molar ratio of 10:1 at a pressure of 2 atm, a temperature of 275° C. and a GHSV of 2500 hr$^{-1}$ for a period of 168 hours.

A slightly modified process for the preparation of ethyl acetate by hydrogenating acetic acid has been reported in EP0372847. In this process, a carboxylic acid ester, such as for example, ethyl acetate is produced at a selectivity of greater than 50% while producing the corresponding alcohol at a selectivity less than 10% from a carboxylic acid or anhydride thereof by reacting the acid or anhydride with hydrogen at elevated temperature in the presence of a catalyst composition comprising as a first component at least one of Group VIII noble metal and a second component comprising at least one of molybdenum, tungsten and rhenium and a third component comprising an oxide of a Group IVB element. However, even the optimal conditions reported therein result in significant amounts of by-products including methane, ethane, acetaldehyde and acetone in addition to ethanol. In addition, the conversion of acetic acid is generally low and is in the range of about 5 to 40% except for a few cases in which the conversion reached as high as 80%.

Copper-iron catalysts for hydrogenolyzing esters to alcohols are described in U.S. Pat. No. 5,198,592. A hydrogenolysis catalyst comprising nickel, tin, germanium and/or lead is described in U.S. Pat. No. 4,628,130. A rhodium hydrogenolysis catalyst that also contains tin, germanium and/or lead is described in U.S. Pat. No. 4,456,775.

Several processes that produce ethanol from acetates, including methyl acetate and ethyl acetate, are known in the literature.

WO8303409 describes producing ethanol by carbonylation of methanol by reaction with carbon monoxide in the presence of a carbonylation catalyst to form acetic acid which is then converted to an acetate ester followed by hydrogenolysis of the acetate ester formed to give ethanol or a mixture of ethanol and another alcohol which can be separated by distillation. Preferably the other alcohol or part of the ethanol recovered from the hydrogenolysis step is recycled for further esterification. Carbonylation can be effected using a $CO/H_2$ mixture and hydrogenolysis can similarly be conducted in the presence of carbon monoxide, leading to the possibility of circulating gas between the carbonylation and hydrogenolysis zones with synthesis gas, preferably a 2:1 $H_2$:CO molar mixture being used as makeup gas.

WO2009063174 describes a continuous process for the production of ethanol from a carbonaceous feedstock. The carbonaceous feedstock is first converted to synthesis gas which is then converted to ethanoic acid, which is then esterified and which is then hydrogenated to produce ethanol.

WO2009009320 describes an indirect route for producing ethanol. Carbohydrates are fermented under homoacidogenic conditions to form acetic acid. The acetic acid is esterified with a primary alcohol having at least 4 carbon atoms and hydrogenating the ester to form ethanol.

US Pub. No. 20110046421 describes a process for producing ethanol comprising converting carbonaceous feedstock to syngas and converting the syngas to methanol. Methanol is carbonylated to ethanoic acid, which is then subjected to a two stage hydrogenation process. First the ethanoic acid is converted to ethyl ethanoate followed by a secondary hydrogenation to ethanol.

US Pub. No. 20100273229 describes a process for producing acetic acid intermediate from carbohydrates, such as corn, using enzymatic milling and fermentation steps. The acetic acid intermediate is acidified with calcium carbonate and the acetic acid is esterified to produce esters. Ethanol is produced by a hydrogenolysis reaction of the ester.

U.S. Pat. No. 5,414,161 describes a process for producing ethanol by a gas phase carbonylation of methanol with carbon monoxide followed by a hydrogenation. The carbonylation produces acetic acid and methyl acetate, which are separated and the methyl acetate is hydrogenated to produce ethanol in the presence of a copper-containing catalyst.

U.S. Pat. No. 4,497,967 describes a process for producing ethanol from methanol by first esterifying the methanol with acetic acid. The methyl acetate is carbonylated to produce acetic anhydride which is then reacted with one or more aliphatic alcohols to produce acetates. The acetates are hydrogenated to produce ethanol. The one or more aliphatic alcohols formed during hydrogenation are returned to the acetic anhydride esterification reaction.

U.S. Pat. No. 4,454,358 describes a process for producing ethanol from methanol. Methanol is carbonylated to produce methyl acetate and acetic acid. The methyl acetate is recovered and hydrogenated to produce methanol and ethanol. Ethanol is recovered by separating the methanol/ethanol mixture. The separated methanol is returned to the carbonylation process.

The need remains for improved processes for efficient ethanol production by reducing esters on a commercially feasible scale.

SUMMARY OF THE INVENTION

In a first embodiment, the present invention is directed to a method of producing ethanol comprising: hydrogenating acetic acid in a first reactor in the presence of a first catalyst to form a hydrogenation product comprising ethyl acetate, water, and acetic acid; recovering an ester feed stream from the hydrogenation product; and reducing the ester feed stream in a second reactor in the presence of a second catalyst to form ethanol; wherein at least 70%, 80% or 90% of the acetic acid is converted and further wherein less than 45% of the acetic acid is converted to ethanol. In some embodiments, the ester feed stream may be recovered in the absence of an esterification process. The hydrogenation product may comprise from 20 to 95 wt. % or from 40 to 95 wt. % ethyl acetate, from 5 to 40 wt. % water, and from 0.01 to 30 wt. % acetic acid. The hydrogenation product may further comprise from 0.1 to 30 wt. % ethanol. In some embodiments, none of the ethanol formed by reducing the ester feed is recycled to the first reactor. The hydrogenation product may be fed to a decanter to be condensed and biphasically separated into an organic phase and an aqueous phase, wherein the organic phase may be the ester feed stream fed to the second reactor. The organic phase may be further separated in an extractive column using at least one extractive agent to obtain an extractant stream and an ethyl acetate rich extractant stream, wherein the ethyl acetate rich extractant stream may be the ester feed stream fed to the second reactor. In some embodiments, the hydrogenation product may be fed directly to a decanter, without any intervening separation. Thus, the hydrogenation product is not distilled prior to the decanter. The ester feed stream may comprise less than 5 wt. % ethanol and water. The second catalyst may comprise a Group VIII-based catalyst or may comprise a copper-based catalyst. The molar ratio of hydrogen to ethyl acetate fed to the second reactor may be from 2:1 to 100:1. The second reactor may be operated at a temperature from 125° C. to 350° C. and a pressure of 700 to 8,500 kPa. The first catalyst may have a selectivity to ethyl acetate that is greater than 50%. The first reactor may be operated at a temperature from 125° C. to 350° C., a pressure of 10 kPa to 5000 kPa, and a hydrogen to acetic acid mole ratio of greater than 4:1. The method may further comprise converting a carbon source into methanol and converting the methanol into the acetic acid, wherein the carbon source may be selected from the group consisting of natural gas, petroleum, biomass, and coal. In some embodiments, a carbon source may be converted into syngas. At least a portion of the syngas may be converted into methanol and then the methanol may be converted into the acetic acid, wherein the carbon source may be selected from the group consisting of natural gas, petroleum, biomass, and coal. In still further embodiments, a carbon source may be converted into syngas. At least a portion of the syngas may be separated into a hydrogen stream and a carbon monoxide stream. At least a portion of the carbon monoxide stream may be reacted with methanol to form the acetic acid, wherein the carbon source is selected from the group consisting of natural gas, petroleum, biomass, and coal. At least a portion of the ester stream may be reduced with at least a portion of the hydrogen stream.

In a second embodiment, the present invention is directed to a method of producing ethanol comprising: hydrogenating acetic acid in a first reactor in the presence of a first catalyst to form a hydrogenation product comprising ethyl acetate, water, and acetic acid; biphasically separating at least a portion of the hydrogenation product in a decanter into an organic phase comprising ethyl acetate and an aqueous phase comprising ethanol and water; and reacting at least a portion of the organic phase with hydrogen in a second reactor to produce ethanol; wherein at least 70% acetic acid is converted and further wherein less than 45% of the acetic acid is converted to ethanol.

In a third embodiment, the present invention is directed to a method of producing ethanol comprising: hydrogenating acetic acid in a first reactor in the presence of a first catalyst to form a hydrogenation product comprising ethyl acetate, water, and acetic acid; biphasically separating at least a portion of the hydrogenation product in a decanter into an organic phase comprising ethyl acetate and an aqueous phase comprising ethanol and water; separating at least a portion of the aqueous phase in a first distillation column to yield a first distillate comprising ethanol and ethyl acetate, and a first residue comprising water; and reacting at least a portion of the organic phase and at least portion of the first distillate with hydrogen in a second reactor to produce ethanol; wherein at least 70% acetic acid is converted and further wherein less than 45% of the acetic acid is converted to ethanol.

In a fourth embodiment, the present invention is directed to a method of producing ethanol comprising: hydrogenating acetic acid in a first reactor in the presence of a first catalyst to form a hydrogenation product comprising ethyl acetate, water, and acetic acid; biphasically separating at least a portion of the hydrogenation product in a decanter into an organic phase comprising ethyl acetate and an aqueous phase comprising ethanol and water; separating at least a portion of the organic phase into an ester-enriched stream and an ethanol-water stream, wherein the ester-enriched stream has a temperature that is at least 70° C.; and reacting at least a portion of the ester-enriched stream with hydrogen in a second reactor to produce ethanol; wherein at least 70% acetic acid is converted and further wherein less than 45% of the acetic acid is converted to ethanol.

In a fifth embodiment, the present invention is directed to a method of producing ethanol comprising: hydrogenating acetic acid in a first reactor in the presence of a first catalyst to form a hydrogenation product comprising ethyl acetate, water, and acetic acid; biphasically separating at least a portion of the hydrogenation product in a decanter into an organic phase comprising ethyl acetate and an aqueous phase comprising ethanol and water; passing the organic phase through at least one membrane to yield a retentate comprising a dry organic phase and a permeate comprising water, wherein the retentate is fed to the second reactor; and reacting at least a portion of the dry organic phase with hydrogen in a second reactor to produce ethanol; wherein at least 70% acetic acid is converted and further wherein less than 45% of the acetic acid is converted to ethanol.

In a sixth embodiment, the present invention is directed to a method of producing ethanol comprising: hydrogenating acetic acid in a first reactor in the presence of a first catalyst to form a hydrogenation product comprising ethyl acetate, water, and acetic acid; biphasically separating at least a portion of the hydrogenation product in a decanter into an organic phase comprising ethyl acetate and an aqueous phase comprising ethanol and water; separating at least a portion of the organic phase in an extractive column using at least one extractive agent to yield an extractant comprising ethyl acetate, and a raffinate comprising ethanol and water; and reacting at least a portion of the extractant with hydrogen in a second reactor to produce ethanol; wherein at least 70% acetic acid is converted and further wherein less than 45% of the acetic acid is converted to ethanol.

In a seventh embodiment, the present invention is directed to a method of producing ethanol comprising: hydrogenating acetic acid in a first reactor in the presence of a first catalyst to produce an ester feed stream; reacting at least a portion of the ester feed stream with hydrogen in a second reactor to produce a crude reaction mixture comprising ethyl acetate, ethanol, and at least one alcohol having at least 4 carbon atoms; separating at least a portion of the crude reaction mixture in a first distillation column to yield a first distillate comprising ethyl acetate and a first residue comprising ethanol; and separating at least a portion of the first residue in a first distillation column to yield an ethanol sidestream and a first residue comprising the at least one alcohol having at least 4 carbon atoms; wherein at least 70% acetic acid is converted and further wherein less than 45% of the acetic acid is converted to ethanol. The ester feed stream may comprise less than 6 wt. % ethanol and less than 5 wt. % water. The at least one alcohol having at least 4 carbon atoms is selected from the group consisting of n-butanol and 2-butanol. The crude reaction mixture may comprise from 0.01 to 2 wt. % 2-butanol. The conversion of ethyl acetate to ethanol in the second reactor may be from 50 to 95%, or from 70 to 85%.

In an eighth embodiment, the present invention is directed to a method of producing ethanol comprising: hydrogenating acetic acid in a first reactor in the presence of a first catalyst to produce an ester feed stream; reacting at least a portion of the ester feed stream with hydrogen in a second reaction zone to produce a crude reaction mixture comprising ethanol, diethyl acetal, and at least one alcohol having at least 4 carbon atoms; and separating at least a portion of the crude reaction mixture in one or more distillation columns to yield an ethanol product, wherein the ethanol product, based on the crude reaction mixture, has a reduced amount of diethyl acetal and a reduced amount of the at least one alcohol having at least 4 carbon atoms; wherein at least 70% acetic acid is converted and further wherein less than 45% of the acetic acid is converted to ethanol.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1B:
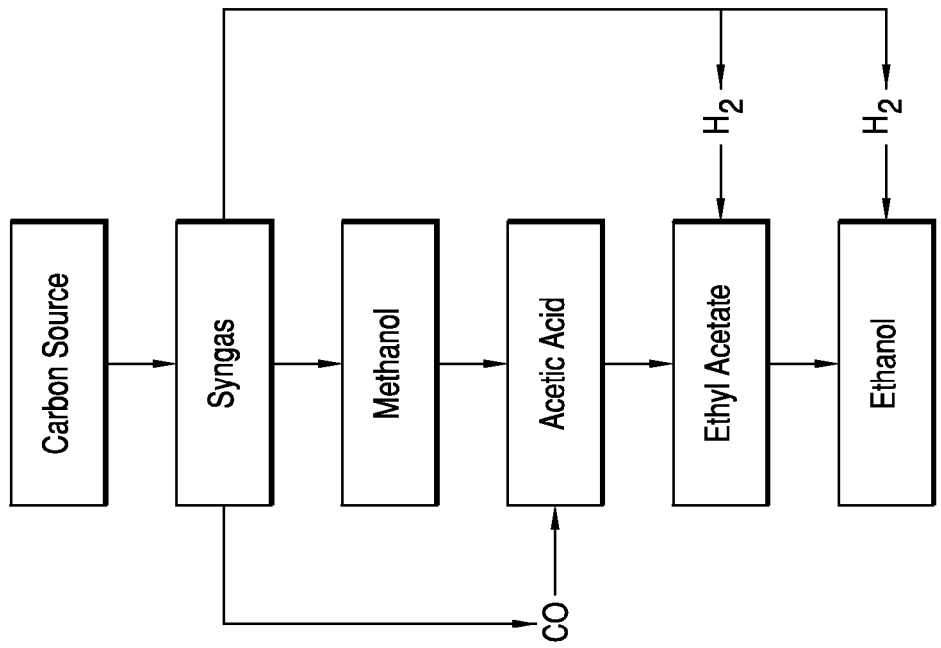
FIGS. 1A and 1B are general flow schemes for producing ethanol from a carbon source in accordance with one embodiment of the present invention.

The present invention relates to processes for producing ethanol from acetic acid through an acetate intermediate, in particular ethyl acetate. In one embodiment, acetic acid is hydrogenated to ethyl acetate and the ethyl acetate is reduced to ethanol. To phase separate the ethyl acetate from the reactor product by hydrogenating acetic acid, it is preferred that the reactor product contain relatively low amounts of acetic acid and/or ethanol. Phase separation may reduce the number of processing steps required to obtain an ethyl acetate feed that is suitable for being reduced. Without limitation, in one embodiment, a decanter may be used to phase separate the reactor product.

In one embodiment, at least 70% of the acetic acid is converted during the hydrogenation reaction, and more preferably at least 85% or at least 90%. Higher conversions are preferred because there will be less acetic acid in the reactor product that may prevent phase separation of the ethyl acetate. In addition, a majority of the acetic acid is converted to ethyl acetate and less than 45% of the acetic acid is converted to ethanol, i.e. the selectivity to ethanol is less than 40%, or less than 35%. Preferably, the selectivity to ethanol is less than 30% or less than 20%. Higher amounts of ethanol in the reactor product may carry over to much water in the ethyl acetate feed and may prevent phasing of the reactor product. The acetic acid conversion and acetic acid selectivity to ethanol may be controlled by the catalyst used in the hydrogenation process.

By reducing the amount of ethanol formed by the hydrogenation of acetic acid, the hydrogenation product may be fed directly to a decanter to separate the hydrogenation product into an organic phase comprising ethyl acetate and an aqueous phase comprising water and ethanol. Once hydrogen and other non-condensable gases are removed, the reactor product is directly fed from the hydrogenation to reactor to the decanter and thus the need for a distillation column for separating acetic acid is eliminated. The elimination of a column between the hydrogenation reaction and decanter may improve process efficiency and decrease costs.

High acetic acid conversion is preferred. In some embodiments, acetic acid conversion is at least 70%, e.g., at least 80%, at least 85%, at least 90%, at least 95% or at least 99%. When acetic acid is fed directly to the decanter, it is difficult to separate from the organic phase. A high amount of acetic acid in the organic phase requires the use of liquid-liquid extraction to separate acetic acid and the extractant, e.g., water, from ethanol and ethyl acetate in the organic phase.

High acetic acid conversion to ethyl acetate is preferred. In some embodiments, acetic acid conversion to ethyl acetate is at least 50%, e.g., at least 60%, at least 70%, at least 80% or at least 90%.

Low conversion of acetic acid to ethanol is preferred. In some embodiments, acetic acid conversion to ethanol is less than 45%, e.g., less than 40%, less than 30%, less than 20% or less than 10%. Generally, when 45% or more of the acetic acid is converted to ethanol, a first distillation column must be used to separate water and ethanol prior to sending reactor product to a decanter. No phasing may occur when the hydrogenation product contains high amounts of ethanol.

In one embodiment, the reactor product which may be suitable for phase separation may also be separated using an extractive separator.

Additionally, another advantage of the invention is that no separate esterification step is required to produce the ethyl acetate. Also, a separate source of ethanol is not required to esterify with the acetic acid. In addition, it may not be necessary to recycle a portion of the produced ethanol.

The process involves at least two different reactions that may form minor amounts of impurities, namely hydrogenation of acetic acid and hydrogenolysis of ethyl acetate. The present invention provides an advantageous method of producing an ester feed from a hydrogenation product so that the ester feed is suitable for hydrogenolysis. Pure ethyl acetate may be less cost effective in producing ethanol than acetic acid, and to provide a cost effective ester feed embodiments of the present invention simplify the acetic acid hydrogenation system and use minimal ethyl acetate separation. In addition, the present invention provides efficient separation processes for recovering ethanol after the hydrogenolysis of ethyl acetate. The processes of the present invention advantageously provide a commercially feasible scale for producing ethanol.

Figure 1A:
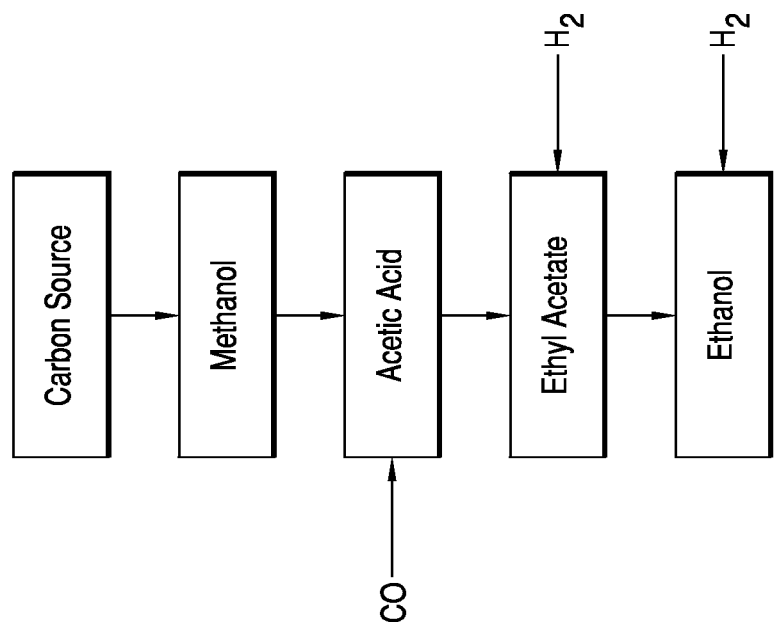

The present invention comprises producing ethanol from acetic acid by hydrogenating the acetic acid to form an ester and reducing the ester. The embodiments of the present invention may also be integrated with methods for producing acetic acid as shown in FIGS. 1A and 1B. For example, acetic acid may be produced from methanol, and thus ethanol production according to embodiments of the present invention may be produced from methanol. In one embodiment, the present invention comprises producing ethanol from methanol by carbonylating the methanol to form acetic acid, hydrogenating the acetic acid to form an ester, and reducing the ester to form ethanol. In yet another embodiment, the present invention comprises producing methanol from syngas, carbonylating the methanol to form acetic acid, hydrogenating the acetic acid to form an ester, and reducing the ester to an alcohol, namely ethanol. In still another embodiment, the present invention comprises producing ethanol from a carbon source, such as coal, biomass, petroleum, or natural gas, by converting the carbon source to syngas, followed by converting the syngas to methanol, carbonylating the methanol to form acetic acid, hydrogenating the acetic acid to form an ester, and reducing the ester to an alcohol. In still another embodiment, the present invention comprises producing ethanol from a carbon source, such as coal, biomass, petroleum, or natural gas, by converting the carbon source to syngas, separating the syngas into a hydrogen stream and a carbon monoxide stream, carbonylating a methanol with the carbon monoxide stream to form acetic acid, hydrogenating the acetic acid to form an ester, and reducing the ester to an alcohol. In addition, the ester may be reduced with the hydrogen stream. Also, methanol may be produced from the syngas.

In particular, the present invention is directed to a process for improving the production of the ester feed to efficiently produce ethanol from the hydrogenolysis process. One obstacle to producing ethanol from ethyl acetate is the thought that pure ethyl acetate needs to be produced as the feed to produce ethanol. Pure ethyl acetate increases production costs and may not achieve desired improvements in the hydrogenolysis process. The present invention provides efficient hydrogenation production costs to result in improvements to the overall ethanol production. Controlling the hydrogenation reactions and separation provide for an efficient production of ester feed stream that has a composition suitable to being reduced to ethanol.

In general, a suitable ester feed stream may be enriched in ethyl acetate, contains less than 5 wt. % ethanol and/or water, and is substantially free of acetic acid. Because no esterification is used, there may be very little ethanol present when recovering the ethyl acetate. For example, reducing the water content in the ester feed stream may improve the recovery of ethanol, and in particular anhydrous ethanol, from the hydrogenolysis reaction. This may reduce the number of distillation columns and separation capital required for the ethanol recovery. However, low finite water concentrations, e.g., less than 5 wt. %, in the ester feed stream may increase ethanol selectivity and/or ethanol productivity in the hydrogenolysis reaction while inhibiting the aldol condensation to higher alcohols, such as propanol and butanol. Not only does water function as a diluent in the hydrogenolysis reaction, but water may effectively slow down the reaction as water competitively binds to the catalyst active sites. Operating the hydrogenation process in a manner that allows for low finite water concentrations reduces the costs for separating in the hydrogenation product while providing an improved benefit in hydrogenolysis to ethanol.

I. Hydrogenation

The hydrogenation reactants, acetic acid and hydrogen, used in connection with the process of this invention may be derived from any suitable source including carbon source such as natural gas, petroleum, coal, biomass, and so forth. Acetic acid may be produced by several methods, including but not limited to, methanol carbonylation, acetaldehyde oxidation, ethylene oxidation, oxidative fermentation, and anaerobic fermentation.

A. Acetic Acid Sources

1. Carbonylation

In one embodiment, the production of ethanol may be integrated with such methanol carbonylation processes. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. A carbonylation system preferably comprises a reaction zone, which includes a reactor, a flasher and optionally a reactor recovery unit. In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt.

Suitable catalysts include Group VIII catalysts, e.g., rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volumes*, Chapter 2.1, p. 27-200, (1$^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068; which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 wppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

A halogen co-catalyst/promoter is generally used in combination with the Group VIII metal catalyst component. Methyl iodide is a preferred halogen promoter. Preferably, the concentration of the halogen promoter in the reaction medium ranges from 1 wt. % to 50 wt. %, and more preferably from 2 wt. % to 30 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

In one embodiment, the temperature of the carbonylation reaction in the reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa. Acetic acid is typically manufactured in a liquid phase reaction at a temperature from about 150° C. to about 200° C. and a total pressure from about 2 to about 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Water may be formed in situ in the reaction medium, for example, by the esterification reaction between methanol reactant and acetic acid product. In some embodiments, water is introduced to the reactor together with or separately from the other components of the reaction medium. Water may be separated from the other components of the reaction product withdrawn from reactor and may be recycled in controlled amounts to maintain the required concentration of water in the reaction medium. Preferably, the concentration of water maintained in the reaction medium ranges from 0.1 wt. % to 16 wt. %, e.g., from 1 wt. % to 14 wt. %, or from 1 wt. % to 3 wt. % of the total weight of the reaction product.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present together. The absolute concentration of iodide ion is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt. % to 30 wt. %, e.g., from 1 wt. % to 25 wt. %, or from 2 wt. % to 20 wt. %; and the lithium iodide may be present in amounts ranging from 5 wt. % to 20 wt. %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reaction zone of the present invention without the need for condensing the acetic acid and light ends or removing water, saving overall processing costs.

2. Direct from Syngas

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenolysis step may be supplied from syngas.

In some embodiments, some or all of the raw materials may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the ethyl acetate to form the crude reaction mixture may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

3. Fermentation to Acetic Acid

In another embodiment, the acetic acid used in the hydrogenation reaction may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii,*

*Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenolysis step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

4. Acetic Acid Feed

The acetic acid feed stream that is fed to the hydrogenation step may also comprise other carboxylic acids and anhydrides, acetaldehyde, and acetone. In one aspect, the acetic acid feed stream comprises one or more of the compounds selected from the group consisting of acetic acid, propionic acid, acetic anhydride, acetaldehyde, ethyl acetate, diethyl acetal, and mixtures thereof. These other compounds may also be hydrogenated in the processes of the present invention. Water may also be present, generally in amounts of less than 10 wt. %, in the acetic acid feed.

B. Hydrogenation Reaction

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethyl acetate may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 350° C., from 250° C. to 325° C., or from 290° C. to 320° C. The pressure may range from 10 kPa to 5000 kPa, e.g., from 500 kPa to 3500 kPa, or from 1000 kPa to 3100 kPa. Higher pressures may be used to favor selectivity to ethyl acetate. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The hydrogenation of acetic acid to form ethyl acetate is preferably conducted in the presence of a hydrogenation catalyst. In one embodiment, the catalyst may favor ethyl acetate over other compounds, such as acetaldehyde or ethanol. Suitable catalysts include those described in U.S. Pat. No. 7,820,852 and U.S. Pub. Nos. 2010/0121114; 2010/0197959; 2010/0197486; and 2011/0098501, the entire contents and disclosure of which is incorporated by reference.

Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIB, VIIB, VIII transition metals, a lanthanide metal, an actinide metal or a metal selected from any of Groups IIIA, IVA, VA, and VIA.

Preferred metal combinations may include nickel/copper, nickel/cobalt, platinum/copper, platinum/cobalt, palladium/copper, palladium/cobalt, nickel/rhenium, platinum/rhenium, palladium/rhenium, nickel/tin, platinum/tin, palladium/tin, nickel/molybdenum, platinum/molybdenum, or palladium/molybdenum.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from nickel, platinum, and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from copper, cobalt, tin, and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

Molar ratios other than 1:1 may be preferred depending on the composition of the catalyst employed. For example, for platinum/tin catalysts, platinum to tin molar ratios less than 0.4:0.6, or greater than 0.6:0.4 are particularly preferred in order to form ethyl acetate from acetic acid at high selectivity, conversion and productivity. More preferably, the Pt/Sn ratio is greater than 0.65:0.35 or greater than 0.7:0.3, e.g., from 0.65:0.35 to 1:0.35 or from 0.7:0.3 to 1:0.3. Selectivity to ethyl acetate may be further improved by incorporating modified supports as described herein.

With rhenium/palladium catalysts, preferred rhenium to palladium molar ratios for forming ethyl acetate in terms of selectivity, conversion and production are less than 0.7:0.3 or greater than 0.85:0.15. A preferred Re/Pd ratio for producing ethyl acetate in the presence of a Re/Pd catalyst is from 0.2:0.8 to 0.4:0.6. Again, selectivity to ethyl acetate may be further improved by incorporating modified supports as described herein.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that utilize a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

In addition to the metal, the catalysts of the first embodiment further comprise a support, optionally a modified support. As will be appreciated by those of ordinary skill in the art, support materials are selected such that the catalyst system is suitably active, selective and robust under the process conditions employed for the formation of ethyl acetate or a mixture of ethyl acetate and ethanol. Suitable support materials may include, for example, stable metal oxide-based supports or ceramic-based supports as well as molecular sieves, such as zeolites. Examples of suitable support materials include without limitation, iron oxide, silica, alumina, silica/aluminas, titania, zirconia, magnesium oxide, calcium silicate, carbon, graphite, high surface area graphitized carbon, activated carbons, and mixtures thereof. Exemplary preferred supports are selected from the group consisting of silica/aluminas, titania, and zirconia.

The supports may further comprise a support modifier. A support modifier is added to the support and is not naturally present in the support. A support modifier adjusts effects of the acidity of the support material. The acid sites, e.g. Brønsted acid sites, on the support material may be adjusted by the support modifier, for example, to favor selectivity to ethyl acetate and mixtures of ethyl acetate during the hydrogenation of acetic acid. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

As indicated, the catalyst support may be modified with a support modifier. In some aspects, the support material is too basic or is not acidic enough for formation of ethyl acetate at high selectivity. In this case, the support may be modified with a support modifier that adjusts the support material by increasing the number or availability of acid sites by using a redox support modifier or an acidic support modifier. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

Without being bound by theory, it is believed that an increase in acidity of the support may favor ethyl acetate formation. However, increasing acidity of the support may also form ethers and basic modifiers may be added to counteract the acidity of the support.

In some aspects, the support material may be undesirably too acidic for formation of ethyl acetate at high selectivity. In this case, the support material may be modified with a basic support modifier. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; a surface area of about 250 $m^2/g$; a median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

In particular, the hydrogenation of acetic acid may achieve favorable conversion of acetic acid and favorable selectivity and productivity to ethyl acetate. For purposes of the present invention, the term "conversion" refers to the amount of acetic acid in the feed that is converted to a compound other than acetic acid. Conversion is expressed as a mole percentage based on acetic acid in the feed. As discussed above, to achieve phasing of the crude reactor product, the conversion is preferably higher. In one embodiment, the acetic acid conversion may be at least 70%, e.g., at least 80%, at least 85%, at least 90%, at least 95% or at least 99%.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethyl acetate, we refer to the ethyl acetate selectivity as 60%. Preferably, the selectivity to ethyl acetate is at least 50%, e.g., at least 60% or at least 80%. The catalyst should general favor selectivity to ethyl acetate over ethanol. However, any ethanol that is produced with ethyl acetate may be carried through the hydrogenolysis process into the ethanol product. Preferably, as indicated above, the selectivity to ethanol is less than 45% so that the reactor product may phase. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethyl acetate, formed during the hydrogenation based on the kilograms of catalyst used per hour. A productivity of at least 100 grams of ethyl acetate per kilogram of catalyst per hour, e.g., at least 400 grams of ethyl acetate per kilogram of catalyst per hour or at least 600 grams of ethyl acetate per kilogram of catalyst per hour, is preferred. In terms of ranges, the productivity preferably is from 100 to 3,000 grams of ethyl acetate per kilogram of catalyst per hour, e.g., from 400 to 2,500 grams of ethyl acetate per kilogram of catalyst per hour or from 600 to 2,000 grams of ethyl acetate per kilogram of catalyst per hour.

In various embodiments of the present invention, the reactor product produced by the hydrogenation process, before any subsequent processing, such as purification and separation, will typically comprise ethanol, water, and one or more organic impurities. Exemplary compositional ranges for the reactor product are provided in Table 1. The "others" identified in Table 1 may include, for example, esters, ethers, aldehydes, ketones, alkanes, and carbon dioxide.

TABLE 1

REACTOR PRODUCT COMPOSITIONS

| Component | Conc. (wt. %) | Conc. (wt. %) | Conc. (wt. %) |
|---|---|---|---|
| Ethyl Acetate | 20 to 95 | 30 to 90 | 50 to 88 |
| Acetic Acid | 0 to 30 | 0.01 to 20 | 0.5 to 10 |
| Water | 5 to 40 | 10 to 30 | 12 to 25 |
| Ethanol | 0.1 to 30 | 1 to 25 | 5 to 15 |
| Others | 0.1 to 10 | 0.1 to 6 | 0.1 to 4 |

In some embodiments, a mixture comprising ethyl acetate, ethanol, and water may be produced. This mixture may contain more ethanol than described in Table 1 above. The mixture may be directly fed to hydrogenolysis zone 102 without separating the ethanol and/or acetic acid. Preferably, the mixture contains very low amounts of acetic acid.

In one embodiment, the reactor product comprises acetic acid in an amount less than 20 wt. %, e.g., less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethyl acetate may also be preferably high, and is preferably greater than 75%, e.g., greater than 85% or greater than 90%. The selectivity to ethanol may be preferably low, and is preferably less than 45%, e.g., less than 40%, less than 30% or less than 20%.

Hydrogenation reaction zone 101 comprises a suitable hydrogenation reactor for producing ethyl acetate and separation vapors according to an embodiment of the invention. As shown, acetic acid is the carbonylation stock in the feed to the hydrogenation reactor 185. Other embodiments the carbonylation stock may comprise mixtures of acetic acid and ethyl acetate.

System 100 comprises hydrogenation reaction zone 101 which comprises reactor 185, hydrogen feed line 186, and acetic acid feed line 187. In some embodiments, acetic acid feed line 187 may comprise water in an amount of up to 25 wt. %. Hydrogen, and acetic acid are fed to a vaporizer 188 to create a vapor feed stream in line 189 that is directed to reactor 185. In one embodiment, lines 186 and 187 may be combined and jointly fed to vaporizer 188. The temperature of the vapor feed stream in line 189 is preferably from 100° C. to 350° C., e.g., from 120° C. to 310° C. or from 150° C. to 300° C. Any feed that is not vaporized is removed from vaporizer 188 and may be discarded via blowdown stream 190. In addition, although line 189 is shown as being directed to the top of reactor 185, line 189 may be directed to the side, upper portion, or bottom of reactor 185.

Figure 2A:
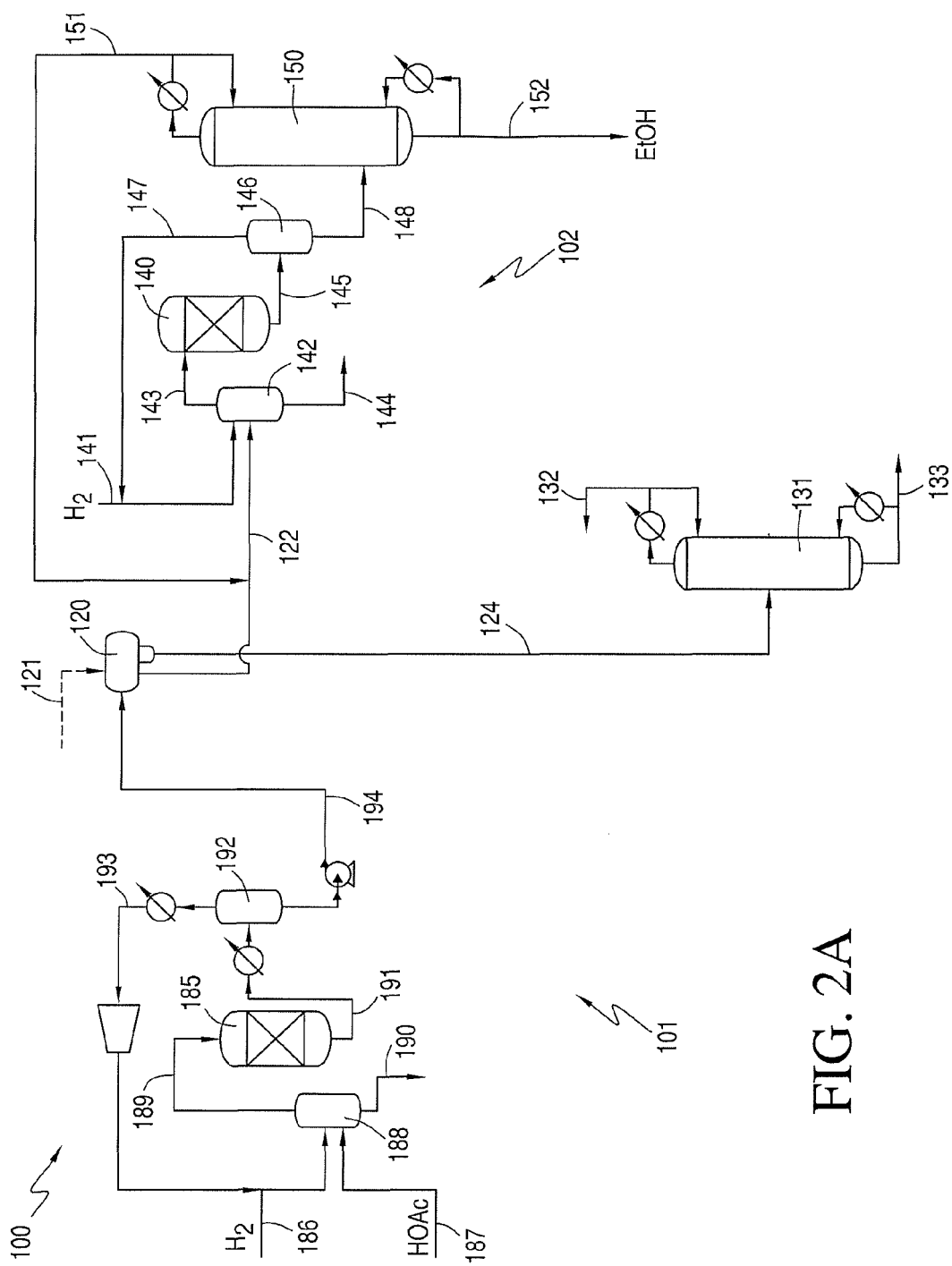
FIG. 2A is a schematic diagram of ethanol production process that directly feeds an organic phase of the product from acetic acid hydrogenation to the hydrogenolysis zone in accordance with one embodiment of the present invention.
Figure 2B:
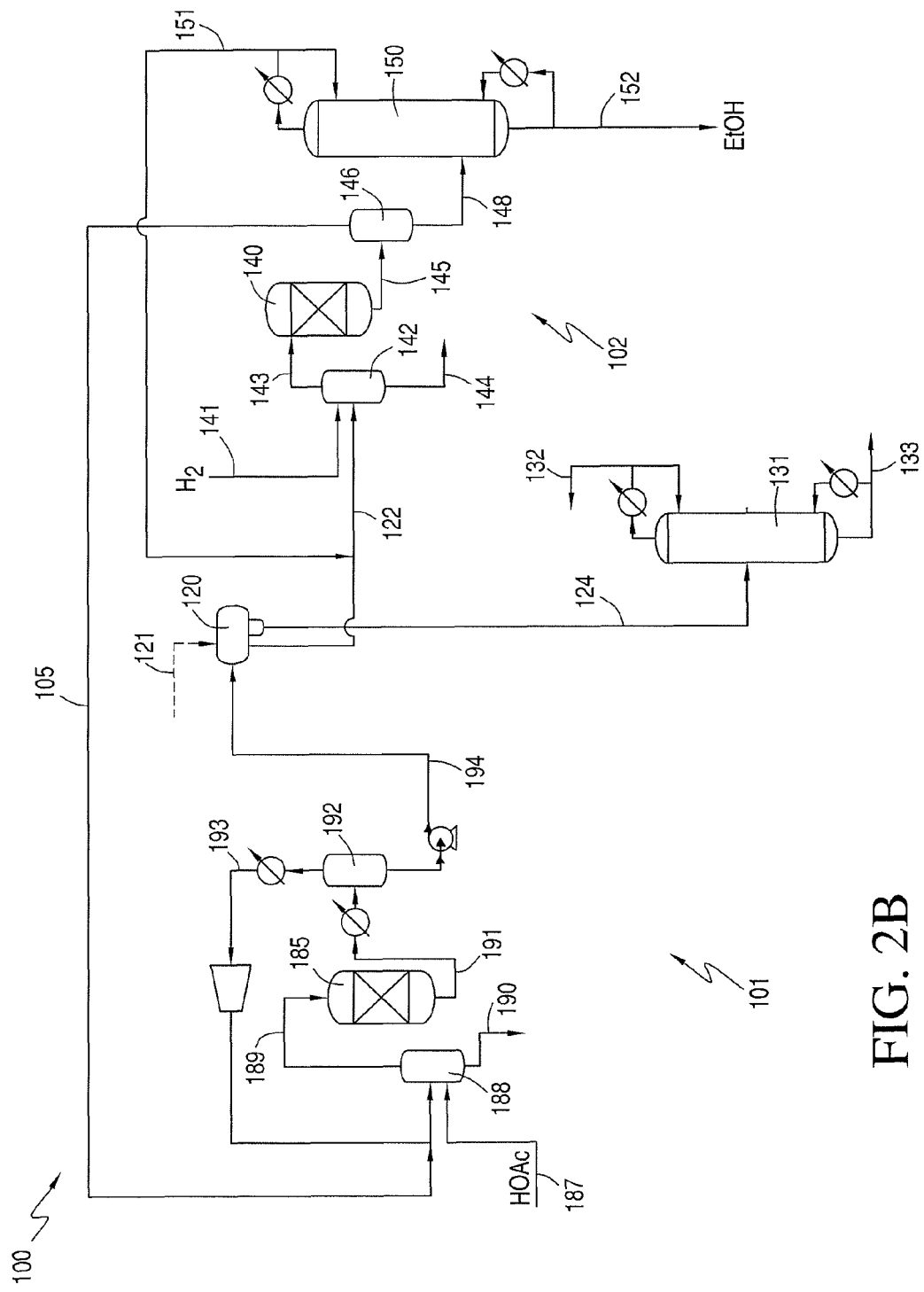
FIG. 2B is a schematic diagram of ethanol production process having a hydrogen recycle from the hydrogenolysis reactor to hydrogenation reactor in accordance with one embodiment of the present invention.

As shown in FIG. 2A, there may be separate sources of hydrogen for the hydrogenation zone 101 and hydrogenolysis zone 102. In FIG. 2B, hydrogen may be introduced to the hydrogenolysis zone 102 and recycled to hydrogenation zone 101 via line 105. For convenience, the other FIGS. of the present invention show separate hydrogen sources as in FIG. 2A, but it is understood that these embodiments could also be used with the hydrogen integration between the zones.

Hydrogenation reactor 185 contains the catalyst that is used in the hydrogenation of the carboxylic acid, preferably acetic acid. In one embodiment, one or more guard beds (not shown) may be used upstream of the reactor to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a reactor product is withdrawn, preferably continuously, from reactor 185 via line 191.

Reactor product in line 191 may be condensed and fed to a separator 192, which, in turn, provides a vapor stream 193 and a liquid stream 194. In some embodiments, separator 192 may comprise a flasher or a knockout pot. The separator 192 may operate at a temperature from 20° C. to 250° C., e.g., from 30° C. to 225° C. or from 60° C. to 200° C. The pressure of separator 192 may be from 50 kPa to 2000 kPa, e.g., from 75 kPa to 1500 kPa or from 100 kPa to 1000 kPa.

Optionally, separator 192 may also include one or more membranes. The reactor product in line 191 may, without condensing, pass through one or more membranes to separate hydrogen and/or other non-condensable gases from the reactor product. Membranes may allow vapor separation of the reactor product. Polymer-based membranes that operate at a maximum temperature of 100° C. and at a pressure of greater than 500 kPa, e.g., greater than 700 kPa, may be used. The membranes may be palladium-based membranes that have high selectivity for hydrogen, such as palladium-based alloy with copper, yttrium, ruthenium, indium, lead, and/or rare earth metals. Suitable palladium-based membranes are described in Burkhanov, et al., "Palladium-Based Alloy Membranes for Separation of High Purity Hydrogen from Hydrogen-Containing Gas Mixtures," *Platinum Metals Rev.*, 2011, 55, (1), 3-12, the entirety of which is incorporated by reference. Efficient hydrogen separation palladium-based membranes generally have high hydrogen permeability, low expansion when saturated with hydrogen, good corrosion resistance and high plasticity and strength during operation at temperatures of 300° C. to 700° C. Because the reactor product may contain unreacted acid, membrane should tolerate acidic conditions, e.g., a pH of less than 5, or a pH of less than 4.

Vapor stream 193 exiting separator 192 may comprise hydrogen and hydrocarbons, which may be purged and/or returned to reaction zone 101. The returned portion of vapor stream 193 may pass through compressor and may be combined with hydrogen feed line 186 and co-fed to vaporizer 188.

C. Ester Purification

Liquid stream 194 from separator 192 in FIG. 2A or 2B may be biphasically separated in a decanter 120. After hydrogenation, the resulting vapors are collected and condensed. Condensing liquid stream 194 may cause phase separation into a low density or lighter phase that is an organic phase rich in ethyl acetate and a more dense or heavier phase that is an aqueous phase rich in water. To further effectuate phasing, decanter 120 may be maintained a temperature from 0 to 40° C. In another embodiment, water may be added to decanter 120 to enhance phase separation via optional line 121. The optional water added to decanter 120 extracts ethanol from the organic phase thereby decreasing the water concentration in the organic phase. In other embodiments, the hydrogenation product in liquid stream 194 may have a molar ratio of ethanol to ethyl acetate from 1:5 to 1:1.1, e.g., from 1:3 to 1:1.4, or from 1:2 to 1:1.25. A suitable molar ratio of ethanol to ethyl acetate to provide phasing may be 1.1:1.25. The low molar ratio of ethanol to ethyl acetate may also affect phasing. In addition, the low molar ratio of ethanol may also reduce the ethanol concentration in the organic phase and thus also reduce the water concentration in the organic phase.

Exemplary organic phase and aqueous phase compositions are provided in Table 2 below. These compositions may vary depending on the type of hydrogenation reaction and hydrogenation catalyst. Regardless of the type of hydrogenation reaction, it is preferred that each phase contains very low concentrations of acetic acid, e.g., less than 600 wppm, e.g., less than 200 wppm or less than 50 wppm. In one embodiment, the organic phase comprises less than 6 wt. % ethanol and less than 5 wt. % water.

TABLE 2

| DECANTER 120 | | | |
|---|---|---|---|
| | Conc. (wt. %) | Conc. (wt. %) | Conc. (wt. %) |
| Organic Phase | | | |
| Ethyl Acetate | 60 to 99.5 | 60 to 97 | 75 to 95 |
| Water | 0.01 to 10 | 0.5 to 8 | 0.5 to 5 |
| Ethanol | 0.01 to 10 | 0.5 to 6 | 0.5 to 5 |

TABLE 2-continued

| DECANTER 120 | | | |
|---|---|---|---|
| | Conc. (wt. %) | Conc. (wt. %) | Conc. (wt. %) |
| Diethyl acetal | <1 | <0.1 | <0.05 |
| $C_3$+ alcohols | <1 | <0.1 | <0.05 |
| Aqueous Phase | | | |
| Water | 60 to 99.5 | 60 to 97 | 75 to 95 |
| Ethyl Acetate | 0.01 to 30 | 0.5 to 25 | 1 to 15 |
| Ethanol | 0.01 to 20 | 0.1 to 15 | 0.5 to 10 |
| Diethyl acetal | <0.1 | <0.01 | <0.001 |
| $C_3$+ alcohols | <1 | <0.1 | <0.05 |

In some embodiments, an organic phase comprising ethyl acetate is removed from decanter 120 via line 122. The organic phase in line 122, or an aliquot portion thereof, may be directly fed as the ester feed stream to hydrogenolysis zone 102 as shown in FIGS. 2A and 2B. In some embodiments, it may be preferred to preheat the organic phase directly fed to hydrogenolysis zone 102.

An aqueous phase comprising water is also removed from decanter 120 via line 124 and sent to recovery column 131, also referred to as the first column. Although a majority of the ethyl acetate is separated in the organic phase, a minor amount, e.g., less than 1%, or less than 0.75%, of the ethyl acetate in the decanter 120 may be withdrawn in the aqueous phase in line 124. In one embodiment, it is desirable to maximize ethyl acetate efficiency by recovering the ethyl acetate to increase the ethyl acetate to ethanol conversion in the hydrogenolysis zone 102. Optionally, a portion of the aqueous phase from the decanter 120 is purged and removed from the system.

Figure 3:
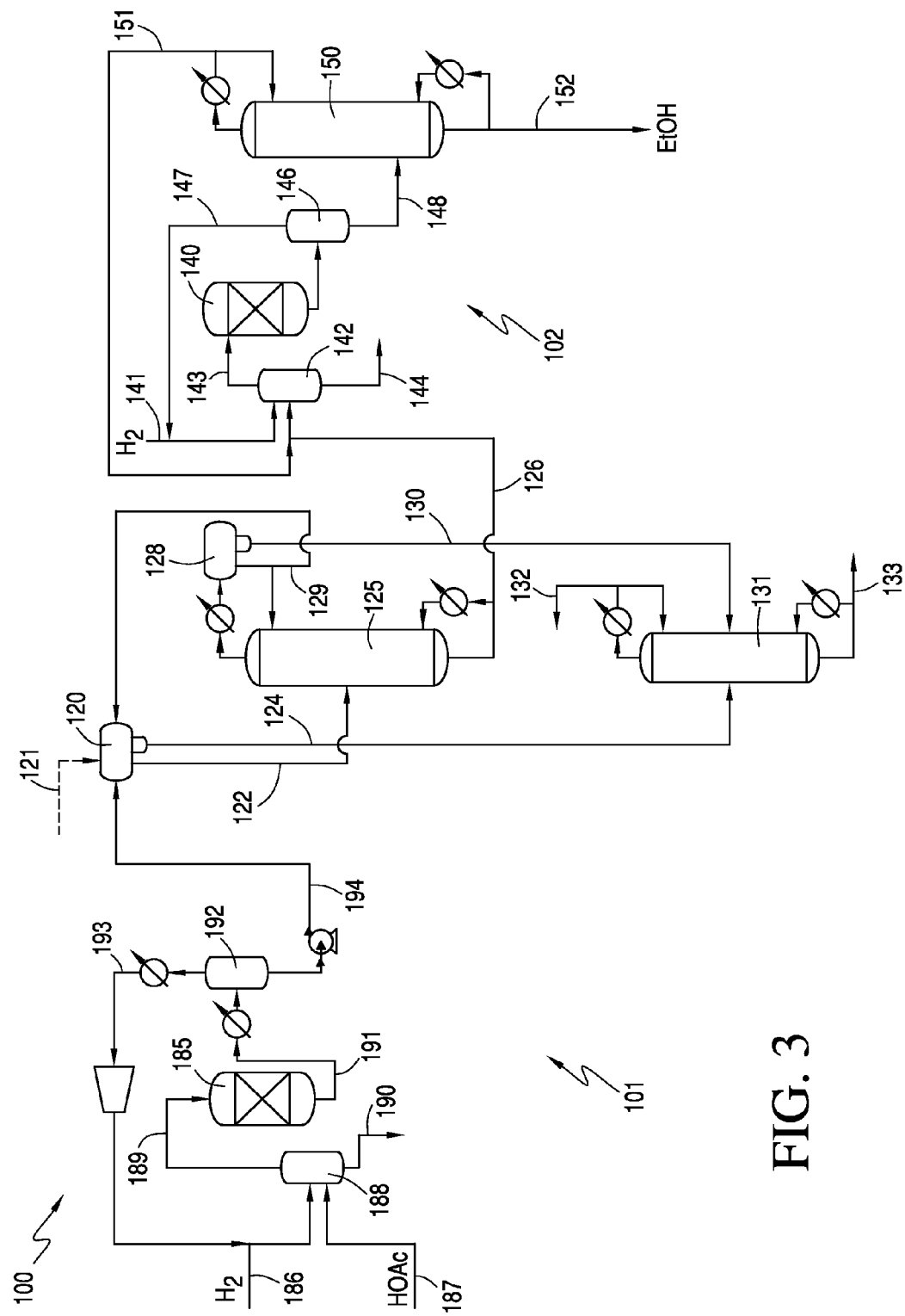
FIG. 3 is a schematic diagram of ethanol production process that uses a purification column to remove water and/or ethanol from the organic phase in accordance with one embodiment of the present invention.
Figure 4:
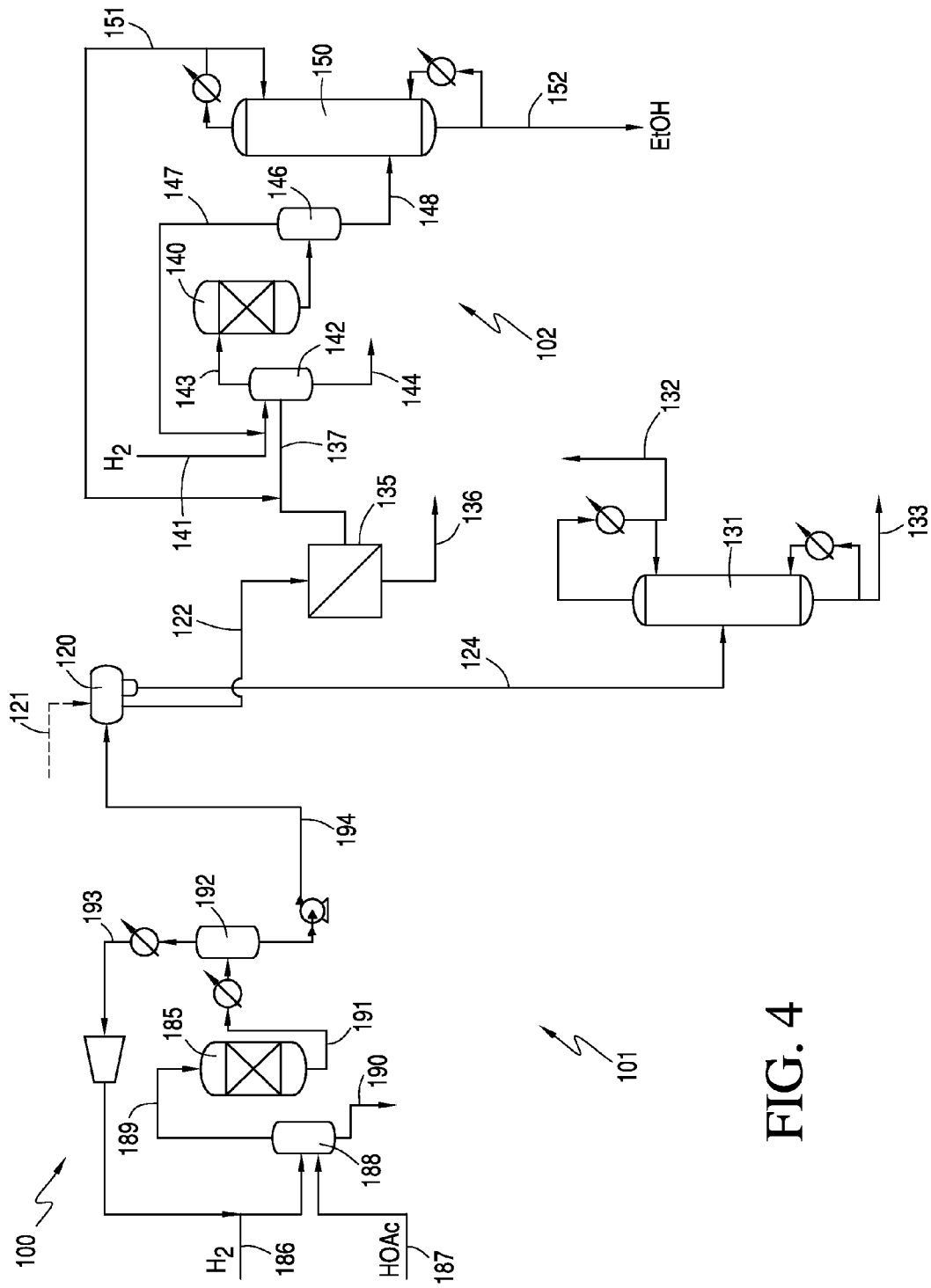
FIG. 4 is a schematic diagram of ethanol production process that uses a membrane unit to remove water from the organic phase in accordance with one embodiment of the present invention.

In some embodiments, it may be desirable to further process the organic phase prior to entering hydrogenolysis zone 102. This may allow feeding a non-aliquot portion of the organic phase to hydrogenolysis zone 102. As shown in FIG. 3, the organic phase may be fed to a purification column 125 to reduce the ethanol and/or water concentrations and remove impurities. In another embodiment, the organic phase may be fed to a membrane separation unit or pervaporization ("pervap") unit 135 to reduce water concentrations as shown in FIG. 4. In further embodiments of the present invention, the organic phase may be fed to a pervap unit 135 and purification column in series.

a. Purification Column

In FIG. 3, purification column 125 removes ethanol and water from ethyl acetate in the organic phase. In particular, column 125 may purify ethyl acetate in the organic phase by removing one or more azeotropes of ethyl acetate. Depending on the composition of organic phase and the phasing in decanter 120, a purification column 125 may be advantageous when the ethanol and/or water concentration in the organic phase exceeds 5 wt. %, e.g., exceeds 8 wt. % or exceeds 10 wt. %. Any water fed to hydrogenolysis zone 102 would be expected to pass through and would need to be removed from the final ethanol if desired. Additional ethanol fed to hydrogenolysis reactor 140 may have less of an impact, but may create capacity restraints and bottlenecking.

Purification column 125 may be a tray or packed column. In one embodiment, purification column 125 is a tray column having from 10 to 80 trays, e.g., from 20 to 60 trays or from 30 to 50 trays. Although the temperature and pressure of purification column 125 may vary, when at 65 kPa the temperature of the overhead preferably is from 70° C. to 100° C., e.g., from 75° C. to 95° C. or from 80° C. to 90° C. The temperature at the base of the purification column 125 preferably is from 80° C. to 110° C., e.g., from 85° C. to 105° C. or from 90° C. to 100° C. In other embodiments, the pressure of purification column 125 may be from 10 kPa to 600 kPa, e.g., from 20 kPa to 400 kPa or from 20 kPa to 300 kPa.

Ethyl acetate is preferably removed as a residue stream, i.e. ester-enriched stream, in line 126 and a portion thereof may be fed to a reboiler. In some embodiments, ethyl acetate may be removed as a sidestream (not shown) from the base of column 125 and a residue may be removed and purged. Residue stream in line 126 preferably has a low concentration of ethanol and/or water, which may be less than 2 wt. % individually or collectively, e.g., less than 1 wt. % or less than 0.1 wt. %. The residue stream in line 126 may be directly fed as the ester feed stream to hydrogenolysis zone 102. In one embodiment, residue stream in line 126 has a higher temperature than the organic phase 122, and thus it may be advantageous to directly feed residue stream in line 126 to hydrogenolysis zone 102 because no further preheating is required. In one exemplary embodiment, residue stream in line 126 may have a temperature that is at least 70° C., e.g., at least 80° C. or 85° C. Advantageously, removing impurities in organic phase may efficiently use energy in the system and reduce capital expenses for additional utility heaters.

The distillate of the purification column 125 is an ethyl acetate-ethanol-water stream and is preferably condensed in line 127 by passing through subcooler before being fed to a decanter 128, in which an organic phase is separated from an aqueous phase. A portion or all of the organic phase in line 129, which comprises ethyl acetate and/or ethanol, may be refluxed to the top of purification column 125. In one embodiment, the reflux ratio is from 0.25:1 to 1:0.25, e.g., from 0.5:1 to 1:0.5 or from 1:1 to 1:2. All or a portion of remaining organic phase in line 129 may also be returned to vaporizer 188, and/or decanter 120 as shown in FIG. 3.

In some optional embodiments, not shown, ethyl acetate may be removed as a sidestream near the base of purification column 125. When ethyl acetate is removed as a side stream, the bottoms stream from purification column 125 is preferably withdrawn and may be recycled to vaporizer 188. The optional bottoms stream comprising ethyl acetate acts as an azeotroping agent to assist in the removal of water produced in reactor 185. In one embodiment, a conductivity meter may be used to monitor the acetic acid concentration in the organic phase. When the concentration of acetic acid is greater than a tolerable level for the hydrogenolysis reactor, a purification column 125 may be used to remove acetic acid in the optional bottom stream.

The aqueous phase may be withdrawn from decanter 128 via line 130 and preferably is fed to recovery column 131. The aqueous phases in lines 124 and/or 130 may be co-fed to recovery column 131 or separately fed to recovery column 131. In one embodiment a portion of the aqueous phase of decanter 128 in line 130 is purged and removed from the system.

b. Recovery Column

Recovery column 131 is operated to remove a significant portion of any organic content in aqueous phase in line 124 prior to purging the water. Recovery column 131 may also remove organics from the aqueous phase in line 130 from the purification column 125. Recovery column 131 may be a tray or packed column. In one embodiment, recovery column 131 is a tray column having from 10 to 80 trays, e.g., from 20 to 75 trays or from 30 to 60 trays. Although the temperature and pressure of recovery column 131 may vary, when at atmospheric pressure the temperature of the overhead preferably is from 60° C. to 85° C., e.g., from 65° C. to 80° C. or from 70° C. to 75° C. The temperature at the base of recovery column 131 preferably is from 92° C. to 118° C., e.g., from 97° C. to 113° C. or from 100° C. to 108° C. In other embodiments, the pressure of recovery column 131 may be from 1 kPa to 300 kPa, e.g., from 10 kPa to 200 kPa or from 10 kPa to 150 kPa.

In one embodiment, any of the feeds to recovery column 131 may be at the top of the tower, i.e. near or into the reflux line. This keeps a sufficient loading on the trays such that the column operates as a stripping tower.

Exemplary first distillate and first residue compositions of recovery column 131 are provided in Table 3 below.

TABLE 3

RECOVERY COLUMN 131

|  | Conc. (wt. %) | Conc. (wt. %) | Conc. (wt. %) |
|---|---|---|---|
| First distillate |  |  |  |
| Ethyl Acetate | 20 to 80 | 35 to 75 | 40 to 55 |
| Water | 5 to 50 | 10 to 40 | 10 to 35 |
| Ethanol | 5 to 50 | 10 to 40 | 10 to 35 |
| $C_3$+ Acetates | <1 | <0.1 | <0.01 |
| $C_3$+ alcohols/ketones | <1 | <0.5 | <0.2 |
| First residue |  |  |  |
| Water | 85 to 99.9 | 90 to 99.9 | 97 to 99.9 |
| Ethyl Acetate | 0.001 to 15 | 0.001 to 5 | 0.01 to 2 |
| Ethanol | 0.001 to 15 | 0.001 to 5 | 0.01 to 2 |
| $C_3$+ Acetates | <1 | <0.1 | <0.01 |
| $C_3$+ alcohols/ketones | <1 | <0.05 | <0.01 |

The first distillate of recovery column 131 in line 132 may be condensed and refluxed, as necessary, to the top of recovery column 131. Depending on the composition of overhead in line 132, the overhead may be returned to vaporizer 188, or co-fed with a portion of the organic phase in line 122 to hydrogenolysis zone 102. When the first distillate in line 132 is fed to hydrogenolysis zone 102, it is preferable to control the total concentration of water such that it is less than 8 wt. % based on the total feed to hydrogenolysis section, e.g., less than 5 wt. % or less than 3 wt. %. In addition, particularly when the stream is relatively small, a portion of the first distillate in line 132 may be purged.

The first residue of recovery column 131, which mainly comprises water, is withdrawn in line 133. The water in line 133 may be purged from the system and optionally sent to waste water treatment. In some embodiments, a portion of the water may be returned to decanter 120 and/or decanter 128 to maintain a desired water concentration for separation, fed as an extractive agent to one or more columns in the system, or used to hydrolyze impurities such as diethyl acetal in the process.

c. Membrane

In some embodiments as shown in FIG. 4, it may be desirable to further process the organic phase to remove water prior to being directed to hydrogenolysis zone 102. A portion of the organic phase in line 122 may pass to a membrane separation unit, or a pervap unit 135. The membrane separation unit or pervap unit may be employed to primarily permeate the water present in the organic phase. This creates a dried organic phase retentate that may be fed as an ester feed stream to hydrogenolysis zone 102. Membrane separation or pervap units are well known to those skilled in the art and are available from, among others, Sulzer Chemtech GmbH and Artisan Industries, Inc.

Suitable membranes include shell and tube membrane modules having one or more porous material elements therein. Non-porous material elements may also be included. The material elements may include a polymeric element such as polyvinyl alcohol, cellulose esters, and perfluoropolymers. Membranes that may be employed in embodiments of the present invention include those described in Baker, et al., "Membrane separation systems: recent developments and future directions," (1991) pages 151-169, Perry et al., "Perry's Chemical Engineer's Handbook," 7th ed. (1997), pages 22-37 to 22-69, the entireties of which are incorporated herein by reference.

In other embodiments, water separation may be facilitated using an adsorption unit, molecular sieves, azeotropic distillation column, or a combination thereof.

Using a membrane separation unit 135 to remove water may provide an advantage over other means of removing water. Preferably at least 60% of the water in the organic phase in line 122 is removed, e.g., at least 75% or at least 90%. The resulting dried organic phase in line 137 preferably comprises less than 2 wt. % water, e.g., less than 1 wt. % water or less than 0.5 wt. % water, and may be either processed further in a purification column 125 as described above in FIG. 3 or directly fed as an ester feed stream to hydrogenolysis zone 102 as shown in FIG. 4. In some embodiments, the pervap unit 135 may also remove additional alcohol from the organic phase. The permeate stream in line 136 preferably comprises water and may be purged from the system, returned to decanter 120 or fed to recovery column 131. When purging permeate water in line 136, it may be combined with bottom in line 133.

In some embodiments, a portion of the dried organic phase in line 137 may be refluxed. In other embodiments, membrane separation unit 135 may be used after extractive column 170 to remove water from the ester stream feed in line 175.

d. Extractive Column

Figure 5:
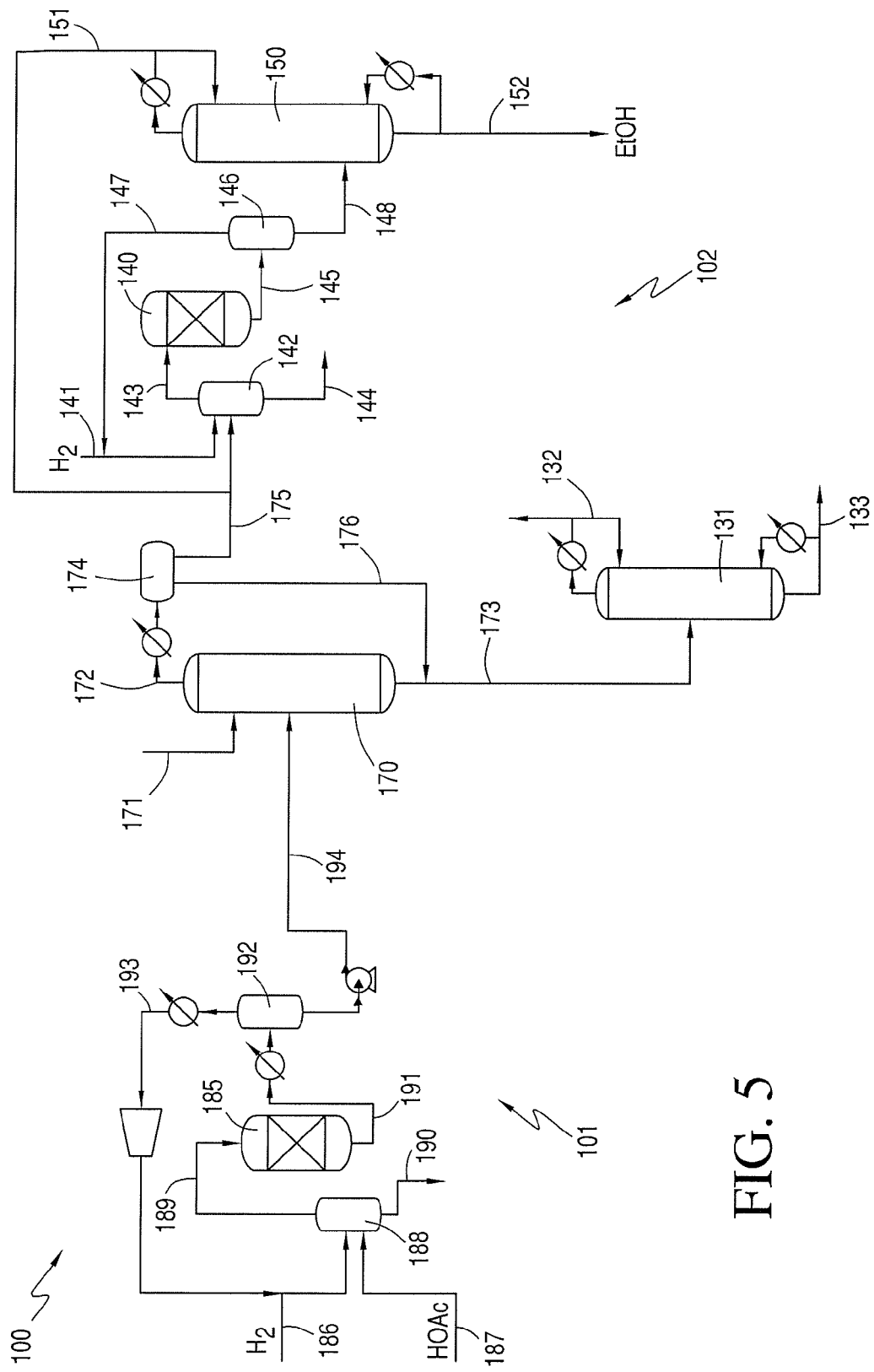
FIG. 5 is a schematic diagram of ethanol production process that uses an extractive column to prepare an ester feed stream for the hydrogenolysis unit in accordance with one embodiment of the present invention.

In another embodiment, an ester feed stream may be recovered from the liquid stream in line 194 using an extractive column 170 as shown in FIG. 5. Extractive column 170 may have one or more trays. Multi-stage extraction may also be used. In one aspect, an extractive column 170 may be used when the ethanol concentration in the hydrogenation product is large. This may be a result of an incomplete conversion in reactor 185 or excess ethanol fed to reactor 185. Optionally, extractive column 170 may be used in combination with decanter 120 and the organic phase may be fed to extractive column 170.

As shown in FIG. 5, liquid stream in line 194 may be condensed and fed to a lower portion of extractive column 170. When extractive column 170 is used, it is not necessary to reflux the condensed liquid stream. In addition to liquid stream, an extractive agent in line 171 is fed at a point above the feedpoint of liquid stream. In one embodiment, extractive agent is fed at a point to allow extractant to be present on a majority of the stages within extractive column 170. The extractive agent preferably comprises water. The feed ratio of extractive agent to liquid stream may be from 5:1 to 1:5, e.g., from 3:1 to 1:3 or 2:1 to 1:2. Extractive column 170 recovers an extractant in line 172 that comprises ethyl acetate and contains less than 5 wt. % water, e.g., less than 4 wt. % water or less than 3 wt. % water. The raffinate in line 173 may comprise water and ethanol may be fed to recovery column 131. A portion of the bottoms from recovery column 131 may be returned to extractive column 170 as the extractive agent.

Extractant in line 172 may be separated, preferably biphasically separated, in a hold up tank 174. Although extractant in line 172 may have very low water concentration, e.g., less than liquid stream, some water may be present. Hold up tank 174 provides sufficient residence time to allow an organic phase in line 175, rich in ethyl acetate, to be separated from extractant in line 172. Organic phase in line 175 comprises low concentrations of water, e.g., of less than 3 wt. %. Optionally an overhead decanter may be used. A portion of organic phase in line 175, or an aliquot portion thereof, may be directly fed as the ester feed stream to hydrogenolysis zone 102 as shown. In some embodiments, it may be preferred to preheat the organic phase directly fed to hydrogenolysis zone 102. An aqueous phase comprising water is also removed from hold up tank 174 via line 176 and combined with raffinate in line 173.

Although the temperature and pressure of extractive column 170 may vary, the temperature of the extracted overhead preferably is from 20° C. to 60° C., e.g., from 25° C. to 55° C. or from 30° C. to 50° C. The temperature at the base of the extractive column 170 preferably is from 20° C. to 60° C., e.g., from 25° C. to 55° C. or from 30° C. to 50° C. In other embodiments, the pressure of extractive column 170 may be from 80 kPa to 400 kPa, e.g., from 90 kPa to 300 kPa or from 100 kPa to 200 kPa.

In some embodiments, the organic phase may be further purified using purification column and/or membrane as described above before being fed to hydrogenolysis zone 102.

II. Hydrogenolysis

In general, the ethyl acetate produced by the hydrogenation reaction zone 101 is fed as the ester feed stream to hydrogenolysis reaction zone 102. As described above, ethyl acetate may be further purified from the hydrogenation product before being fed to hydrogenolysis reaction zone 102. In addition, although acetic acid may not be separated from the hydrogenation product, the process preferably is controlled such that the ester feed stream comprises less than 1 wt. % acetic acid, e.g., less than 0.1 wt. %, or less than 0.01 wt. %.

The amount of ethanol and/or water, if any, in the ester feed stream depends on the purification of the ester feed stream as described above. Preferably, the ester feed stream comprises less than 6 wt. % ethanol, e.g., less than 5 wt. % or less than 2 wt. %. The ester feed stream may also comprises less than 8 wt. % water, e.g., less than 5 wt. % or less than 3 wt. %.

A. Hydrogenolysis Reaction

As shown in FIG. 2, the organic phase in line 122 is referred to as the ester feed stream. In one embodiment, the ester feed stream 122 and hydrogen via feed line 141 are separately introduced into a vaporizer 142 to create a vapor feed stream in line 143 that is directed to hydrogenolysis reactor 140. In one embodiment, lines 122 and 141 may be combined and jointly fed to vaporizer 142. A vapor feed stream in line 143 is withdrawn from vaporizer 142 and is preheated by passing through a heat exchanger. The temperature of the vapor feed stream in line 143 after passing through the heat exchanger is preferably from 100° C. to 350° C., e.g., from 200° C. to 325° C. or from 250° C. to 300° C. Vaporizer 142 preferably operates at a pressure from 700 to 8,500 kPa, e.g., from 1,500 to 7,000 kPa, or from 2,000 to 6,500 kPa. Any feed that is not vaporized is removed from vaporizer 142 as a blowdown stream 144. Blowdown stream 144 may be discarded from the hydrogenolysis zone 102.

Although vapor feed stream in line 143 is shown as being directed to the top of hydrogenolysis reactor 140, line 143 may be directed to the side, upper portion, or bottom of hydrogenolysis reactor 140.

Hydrogen fed to hydrogenolysis reactor 140 may be obtained from syngas. In addition, hydrogen may also originate from a variety of other chemical processes, including ethylene crackers, styrene manufacturing, and catalytic reforming. Commercial processes for purposeful generation of hydrogen include autothermal reforming, steam reforming and partial oxidation of feedstocks such as natural gas, coal, coke, deasphalter bottoms, refinery residues and biomass.

Hydrogen may also be produced by electrolysis of water. In one embodiment, the hydrogen is substantially pure and contains less than 10 mol. % carbon monoxide and/or carbon dioxide, e.g., less than 5 mol. % or less than 2 mol. %.

In one embodiment, the molar ratio of hydrogen to ethyl acetate that is introduced into hydrogenolysis reactor 140 is greater than 2:1, e.g. greater than 4:1, or greater than 12:1. In terms of ranges the molar ratio may be from 2:1 to 100:1, e.g., 4:1 to 50:1, or from 12:1 to 20:1. Without being bound by theory, higher molar ratios of hydrogen to ethyl acetate, preferably from 8:1 to 20:1, are believed to result in high conversion and/or selectivity to ethanol.

Hydrogenolysis reactor 140 may comprise any suitable type of reactor, such as a fixed bed reactor or a fluidized bed reactor. Hydrogenolysis reactions are exothermic and in many embodiments, an adiabatic reactor may be used for the hydrogenolysis reactor. Adiabatic reactors have little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used.

In preferred embodiments, a catalyst is employed in a fixed bed reactor, e.g., in the shape of a pipe or tube, where the reactants, typically in vapor form, are passed over or through the catalyst. Other reactors, such as fluid or ebullient bed reactors, can be employed. In some instances, a hydrogenolysis catalyst may be used in conjunction with an inert material to regulate the pressure drop of the reactant stream through the catalyst bed and the contact time of the reactant compounds with the catalyst particles.

The hydrogenolysis process may be operated in a vapor phase, or a mixed vapor/liquid phase regime. The mixed vapor/liquid phase regime is where the reactant mixture in line 143, at the reactor conditions, is below the dew point temperature. The hydrogenolysis reaction may change from a mixed vapor/liquid phase to a fully vapor phase reaction, as the reaction proceeds down the reactor. The mixed phase hydrogenolysis may also be conducted in other types of reactors, or within a combination of different reactors, for example in a slurry or stirred tank reactor with, or without, external circulation and optionally operated as a cascade or stirred tank, a loop reactor or a Sulzer mixer-reactor. The hydrogenolysis process may be conducted in batch, semi-continuous, or continuous mode. For industrial purposes, continuous mode of operation is the most efficient.

In some embodiments, the hydrogenolysis reactor may comprise other types of reactors, such as fluidized bed, spinning basket and buss loop, or heat exchanger reactors. A mixed vapor/liquid phase hydrogenolysis reaction can be conducted with co-flow or counterflow of the vapor, e.g., hydrogen, to the liquid, i.e. ester feed stream, in a bubble reactor. Trickle bed reactors may also be used.

In one embodiment, a heterogeneous catalyst is used in hydrogenolysis reactor 140. The catalyst may be a copper-based catalyst. Copper-based catalyst may comprise copper chromite, copper and zinc, and/or copper-zinc-oxide. Other copper-based catalyst may include an MgO—SiO$_2$ support that is impregnated with copper. Mixed copper oxide based catalyst may include copper and a second metal selected from zinc, zirconium, manganese, and/or oxides thereof. In some embodiments, aluminum oxide may also be present in the catalyst. The presence of aluminum oxide is believed to increase the heavy alcohol, and/or ketone concentrations during the reduction of ethyl acetate due to the presence of acidic sites. In those embodiments, the catalyst may comprise a basic component, such as magnesium or calcium, to reduce the acidic sites or the aluminum oxide concentration may be very low, e.g., less than 0.1 wt. %. In some embodiments, the catalyst may be substantially free of aluminum oxide.

A suitable copper-based catalyst may comprises from 30 to 70 wt. % copper oxide, 15 to 45 wt. % zinc oxide, and/or 0.1 to 20 wt. % aluminum oxide. More preferably, a copper-based catalyst may comprises from 55 to 65 wt. % copper oxide, 25 to 35 wt. % zinc oxide, and/or 5 to 15 wt. % aluminum oxide. Preferably, the copper-based catalyst is supported on zinc oxide and preferably comprises from 20 to 40 wt. % of copper, in terms of the metal content.

In other embodiments, the catalyst employed in hydrogenolysis reactor 140 may be a Group VIII-based catalyst. Group VIII-based catalyst may comprise a Group VIII metal selected from the group consisting of iron, ruthenium, osmium, cobalt, rhodium, iridium, nickel, palladium, and platinum. In addition, there may be one or more secondary promoter metals selected from the group consisting of zinc, cobalt, tin, germanium, lead, rhenium, tungsten, molybdenum. Group VIII-based catalysts may advantageously be supported on any suitable support known to those skilled in the art; non-limiting examples of such supports include carbon, silica, titania, clays, aluminas, zinc oxide, zirconia and mixed oxides. Preferably, the palladium based catalyst is supported on carbon. In addition, the Group VIII-based catalyst may be supported on any suitable support, such as silica, silica-alumina, calcium metasilicate, carbon, titania, clays, aluminas, zinc oxide, zirconia, and mixed metal oxides. For example, palladium based catalysts may be supported on carbon.

The reduction of ethyl acetate to produce ethanol, e.g., in the hydrogenolysis reactor 140, is typically conducted at elevated temperatures from 125° C. to 350° C., e.g., from 180° C. to 345° C., from 225° C. to 310° C., or from 290° C. to 305° C. Reaction temperatures greater than 240° C., or greater than 260° C., may increase conversion of ethyl acetate. Although not bound by theory, it is believed that reduced temperatures in the hydrogenolysis reactor of less than 275° C. may suppress the formation of heavy impurities such as alcohols and/or ketones. The pressure in the hydrogenolysis reactor may operate under high pressure of greater than 1000 kPa, e.g., greater than 3,000 kPa or greater than 5,000 kPa. In terms of ranges the pressure in the hydrogenolysis reaction may be from 700 to 8,500 kPa, e.g., from 1,500 to 7,000 kPa, or from 2,000 to 6,500 kPa. Pressure greater than 2,500 kPa may be more favorable for improving ethanol productivity and/or selectivity. The reactants may be fed to hydrogenolysis reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 20,000 hr$^{-1}$, e.g., from 1000 hr$^{-1}$ to 10,000 hr$^{-1}$, or from 2000 hr$^{-1}$ to 7,000 hr$^{-1}$.

In particular, the reaction of ethyl acetate may achieve favorable conversion of ethyl acetate and favorable selectivity and productivity to ethanol. For purposes of the hydrogenolysis reactor zone 102, the term "conversion" refers to the amount of ethyl acetate in the feed that is converted to a compound other than ethyl acetate. Conversion is expressed as a mole percentage based on ethyl acetate in the feed. The conversion may be at least 50%, e.g., at least 70%, at least 90%. In terms of ranges, the conversion of ethyl acetate may range from 50 to 98%, e.g., from 60 to 95% or from 70 to 90%. Although catalysts and reaction conditions that have high conversions may be possible, such as greater than 90% or greater than 95%, in some embodiments a low conversion may be acceptable at high selectivity for ethanol. Compensating for low conversion by appropriate recycle streams or use of larger reactors may be easier than compensating for poor selectivity to ethanol.

Selectivity is expressed as a mole percent based on converted ethyl acetate. It should be understood that each compound converted from ethyl acetate has an independent selectivity and that selectivity is independent from conversion. For example, if 90 mole % of the converted ethyl acetate is converted to ethanol, we refer to the ethanol selectivity as 90%. The selectivity to ethanol is preferably at least 80%, e.g., at least 90% or at least 95%.

The term "productivity," as used herein, refers to the grams of a specified product, e.g., ethanol, formed during the hydrogenolysis, based on the kilograms of catalyst used per hour. A productivity of at least 100 grams of ethanol per kilogram of catalyst per hour, e.g., at least 500 grams of ethanol per kilogram of catalyst per hour or at least 1,000 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

A crude reaction mixture is preferably withdrawn continuously from hydrogenolysis reactor 140 via line 145. Any water in ester feed stream may pass through the hydrogenolysis reactor and be present in a similar amount in the crude reaction mixture. The composition of the crude reaction mixture may vary depending on the ester feed stream, conversion, and selectivity. Exemplary crude reaction mixtures, excluding hydrogen and other gases such as methane, ethane, carbon monoxide and/or carbon dioxide, are shown in Table 4 below.

TABLE 4

CRUDE REACTION MIXTURE

| Component | Conc. (wt. %) | Conc. (wt. %) | Conc. (wt. %) |
|---|---|---|---|
| Ethanol | 35 to 95 | 40 to 85 | 50 to 80 |
| Ethyl Acetate | 0.5 to 40 | 1 to 30 | 1 to 25 |
| Water | 0.001 to 10 | 0.001 to 5 | 0.001 to 3 |
| Aldehyde | <2 | 0.001 to 1.5 | 0.01 to 1 |
| Acetic Acid | <0.5 | <0.01 | <0.001 |
| Diethyl acetal | <1 | <0.1 | <0.05 |
| n-butanol | <1 | <0.5 | <0.1 |
| 2-butanol | 0.01 to 2 | 0.05 to 1.5 | 0.1 to 1 |
| Iso-propanol | <1 | <0.1 | <0.05 |
| Acetone | <1 | <0.5 | <0.1 |
| Heavies | <1 | <0.5 | <0.1 |
| Carbon Gases | 0.1 to 10 | 0.01 to 5 | 0.01 to 3 |

Heavies in Table 5 include organic compounds that have a larger molecular weight than ethanol, such as n-butyl acetate, sec-butyl acetate, ethyl butyrate, isopropyl acetate, 2-methyl-1-propanol, etc. Other acetates, aldehydes, and/or ketones may also be encompassed by heavies. The carbon gases refers to any carbon containing compound that is a gas at standard temperature and pressure, such as carbon monoxide, carbon dioxide, methane, ethane, etc. In one embodiment, the hydrogenolysis reaction is controlled to maintain low impurity concentrations of acetone, n-butanol, and 2-butanol.

B. Separation

The crude reaction mixture in line 145 may be condensed and fed to a separator 146, which, in turn, provides a vapor stream 147 and a liquid stream 148. In some embodiments, separator 146 may comprise a flasher or a knockout pot. Although one separator 146 is shown, there may be multiple separators in some embodiments of the present invention. The separator 146 may operate at a temperature from 20° C. to 250° C., e.g., from 30° C. to 225° C. or from 60° C. to 200° C. The pressure of separator 146 may be greater than 1000 kPa, e.g., greater than 3,000 kPa or greater than 5,000 kPa. In terms of ranges the pressure in the separator may be from 700 to 8,500 kPa, e.g., from 1,500 to 7,000 kPa, or from 2,000 to 6,500 kPa.

Vapor stream 147 exiting separator 146 may comprise hydrogen, carbon monoxide, carbon dioxide, and hydrocarbons, and may be purged and/or returned to hydrogenolysis reactor 140. In some embodiments, the returned vapor stream 147 may be compressed before being combined with hydrogen feed 141. Vapor stream 147 may comprise inert gases, such as nitrogen, or nitrogen may be fed to vapor stream 147 to increase molecular weight for improved polytropic compression requirements. Vapor stream 147 may be combined with the hydrogen feed 141 and co-fed to vaporizer 142.

As shown in FIG. 2B, vapor stream 105 may be returned to hydrogenolysis zone 101.

Figure 7A:
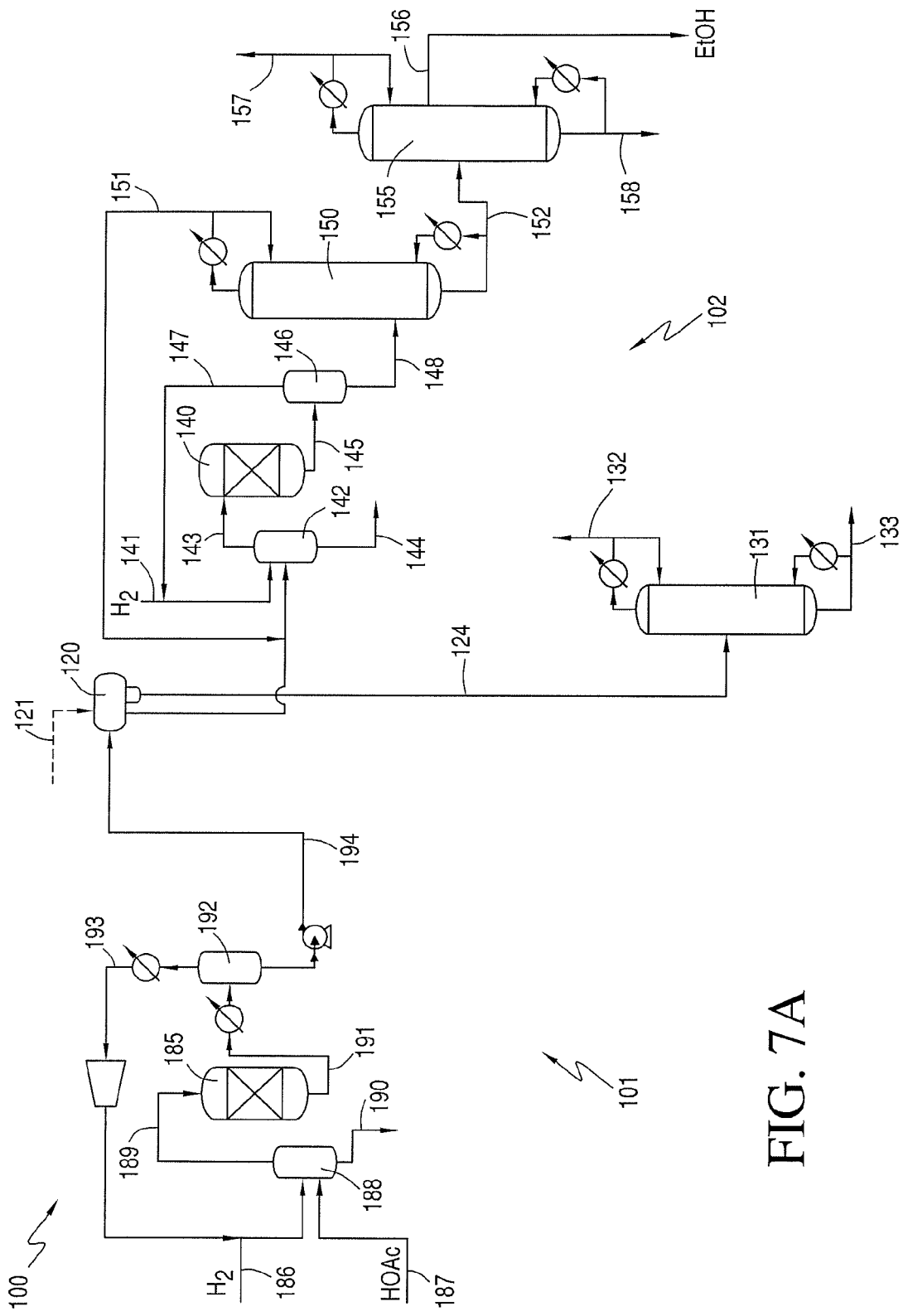
FIG. 7A is a schematic diagram of ethanol production process having a finishing column in the hydrogenolysis zone in accordance with one embodiment of the present invention.
Figure 7B:
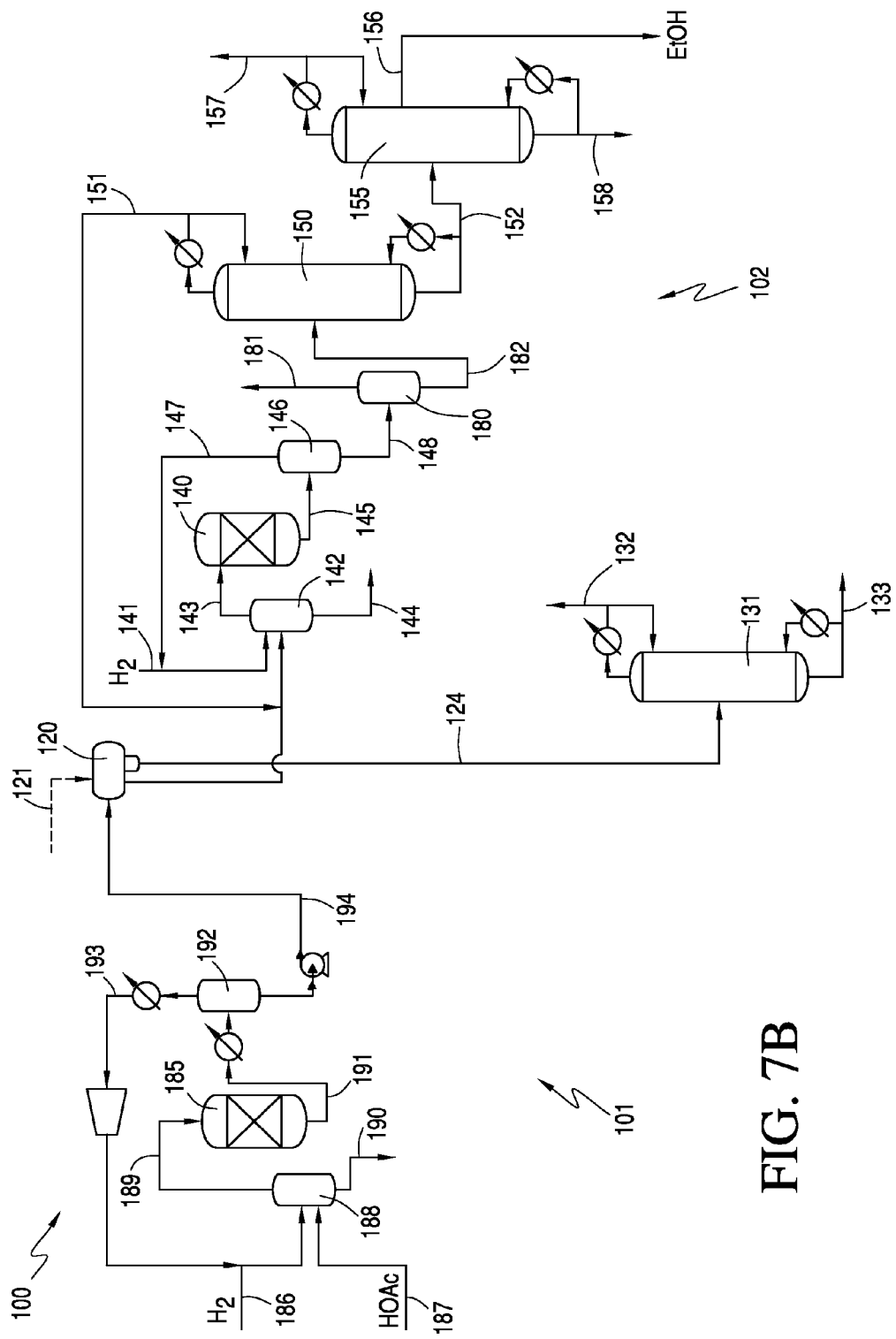
FIG. 7B is a schematic diagram showing multiple flashers in the hydrogenolysis zone in accordance with one embodiment of the present invention.

In one embodiment, the crude reaction mixture in line 145 may be separated using one or more flashers as shown in FIG. 7B. When dual flashers are used, it is preferred to use a high pressure flasher 146 followed by a low pressure flasher 180. The first high pressure flasher 146 operates at the temperature and reaction pressures described above. The second low pressure flasher 180 operates at a temperature from 20° C. to 100° C., e.g., from 30° C. to 85° C. or from 40° C. to 70° C. In one embodiment, the temperature of second flasher 180 preferably is at least 50° C. lower than first flasher 146, e.g., at least 75° C. lower or at least 100° C. lower. The pressure of second flasher 180 preferably is from 0.1 kPa to 1000 kPa, e.g., from 0.1 kPa to 500 kPa or from 0.1 kPa to 100 kPa. In one embodiment, the pressure of second flasher 180 preferably is at least 50 kPa lower than first flasher 146, e.g., at least 100 kPa lower or at least 600 kPa lower. The vapor stream 181 exiting the second flasher 180 may comprise hydrogen and hydrocarbons, which may be purged and/or returned to the reaction zone in a manner similar to that of the first flasher. The liquid stream in line 182 may be fed to the second distillation column 150. Dual flashers may be used in any of the hydrogenolysis zones described herein.

In FIG. 2A, the liquid stream 148 from separator 146 is withdrawn and pumped to the side of a second distillation column 150, also referred to as a "light ends column," to yield a second distillate in line 151 comprising ethyl acetate and a second residue in line 152 comprising ethanol. Preferably the distillation column operates to maintain a low concentration of ethyl acetate in the residue, e.g., less than 1 wt. %, less than 0.1 wt. % or less than 0.01 wt. %. The distillate of column 150 preferably is refluxed at a ratio sufficient to maintain low concentrations of ethyl acetate in the residue and minimize ethanol concentrations in the distillate, and reflux ratio may vary from 30:1 to 1:30, e.g., from 10:1 to 1:10 or from 5:1 to 1:5.

Distillation column 150 may be a tray column or packed column. In one embodiment, distillation column 150 is a tray column having from 5 to 110 trays, e.g., from 15 to 90 trays or from 20 to 80 trays. Distillation column 150 operates at a pressure ranging from 20 kPa to 500 kPa, e.g., from 50 kPa to 300 kPa or from 80 kPa to 200 kPa. Without being bound by theory, lower pressures of less than 100 kPa or less than 70 kPa, may further enhance separation of liquid stream 148. Although the temperature of distillation column 150 may vary, when at atmospheric pressure, the temperature of the distillate exiting in line 151 preferably is from 40° C. to 90° C., e.g., from 45° C. to 85° C. or from 50° C. to 80° C. The temperature of the residue exiting in line 152 preferably is from 45° C. to 95° C., e.g., from 50° C. to 90° C. or from 60° C. to 85° C.

Exemplary compositions of the third column 150 are shown in Table 5 below. It should be understood that the distillate and residue may also contain other components, not listed in Table 5.

TABLE 5

THIRD COLUMN 150

|  | Conc. (wt. %) | Conc. (wt. %) | Conc. (wt. %) |
|---|---|---|---|
| Second distillate |  |  |  |
| Ethyl Acetate | 20 to 80 | 25 to 75 | 30 to 70 |
| Ethanol | 0.01 to 45 | 1 to 35 | 2 to 30 |
| Water | <10 | <5 | <3 |
| Acetaldehyde | 0.01 to 30 | 0.1 to 20 | 1 to 10 |
| Isopropanol | 0.001 to 0.5 | 0.001 to 0.1 | 0.001 to 0.05 |
| Acetone | 0.001 to 3 | 0.001 to 1 | 0.001 to 0.5 |
| Diethyl acetal | 0.001 to 3 | 0.001 to 1 | 0.01 to 0.5 |
| Carbon Gases | 0.001 to 2 | 0.001 to 1 | 0.001 to 0.5 |
| Second residue |  |  |  |
| Ethanol | 80 to 99.5 | 85 to 99.5 | 90 to 99.5 |
| Water | <20 | 0.001 to 15 | 0.01 to 10 |
| Ethyl Acetate | <0.01 | <0.001 | <0.0001 |
| Isopropanol | 0.001 to 3 | 0.001 to 1 | 0.001 to 0.5 |
| Acetone | 0.001 to 3 | 0.001 to 1 | 0.001 to 0.5 |
| Diethyl acetal | 0.001 to 3 | 0.001 to 1 | 0.01 to 0.5 |
| 2-butanol | 0.001 to 3 | 0.01 to 1 | 0.01 to 0.5 |
| n-butanol | <1 | <0.5 | <0.1 |
| Heavies | <1 | <0.5 | <0.1 |

Without being bound by theory, the presence of acetaldehyde in the crude reaction mixture from the hydrogenolysis reactor may produce several different impurities. The heavy impurities, such as higher alcohols, may build up in the second residue. In particular, 2-butanol has been found to be an impurity in this process. The weight ratio of 2-butanol to n-butanol in the second residue may be greater than 2:1, e.g., greater than 3:1 or greater than 5:1. Depending on the intended use of ethanol, these impurities may be of less significance. However, when a purer ethanol product is desired, a portion of second residue may be further separated in a finishing column 155 as described below in FIGS. 7A and 7B.

1. Second Distillate to Recycle to Hydrogenolysis Section

Second distillate in line 151 may comprise ethyl acetate and/or ethanol. In one embodiment, second distillate in line 151 may be returned, directly or indirectly, to hydrogenolysis reactor 140. When hydrogenolysis reactor 140 operates at a lower ethyl acetate conversion, e.g. less than 90% conversion, less than 85% conversion or less than 70% conversion, it may be possible to recycle ethyl acetate back to hydrogenolysis reactor 140. Second distillate in line 151 is condensed and combined with the ester feed stream and co-fed to vaporizer 142. This produces a distillate having a molar ratio of ethanol to ethyl acetate, of approximately 1:1. Advantageously, this embodiment may avoid recycling ethanol through hydrogenolysis reactor 140 that may lead to capacity restraints and additional capital costs. When returning second distillate to hydrogenolysis reactor 140, it is preferred to operate column 150 with a design and under conditions that minimize the ethanol to ethyl acetate ratio, e.g., distillation trays and/or reflux ratio.

In one embodiment, second distillate in line 151 may comprise other organic compounds such as aldehydes. Recycling the aldehydes to hydrogenation reactor 185, may produce additional ethanol. Also, recycling second distillate in line 151 that contains aldehydes to hydrogenolysis reactor 140 tends to produce additional ethanol.

Second residue in line 152 may be withdrawn as the product. When reducing ethyl acetate in the presence of hydrogen, two moles of ethanol are formed. In esterification processes, it is feasible to return a portion of the ethanol to the esterification to produce additional ethyl acetate while still producing ethanol product. In embodiments of the present invention, no ethanol is need for recycling because all the ethyl acetate is produced by hydrogenation. Although, in some optional embodiments, a portion of second residue in line 152 may be separated into an optional ethanol return stream, it is generally preferred to recover the ethanol from the hydrogenolysis zone 102 as the product.

2. Second Distillate to Recycle Hydrogenation Zone

Figure 6:
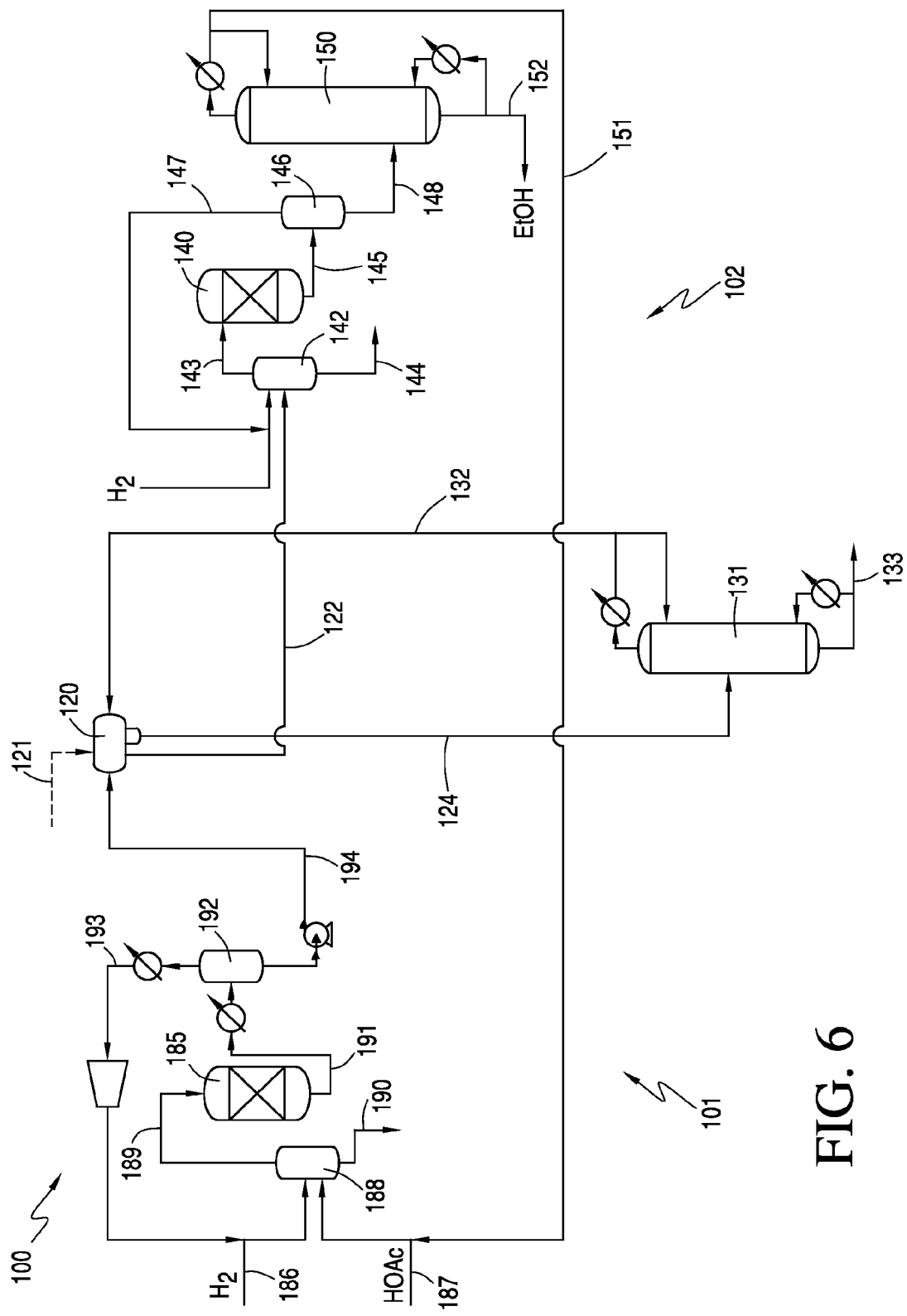
FIG. 6 is a schematic diagram of ethanol production process where the distillate of the light ends column in the hydrogenolysis unit is fed to the azeotrope column in accordance with one embodiment of the present invention.

In another embodiment, as shown in FIG. 6, second distillate in line 151 may be returned, directly or indirectly, to hydrogenation zone 101. Second distillate in line 151 may be combined with the acetic acid feed stream in line 187. When second distillate 151 is returned to hydrogenation reactor 185, it may be possible to return ethyl acetate and some ethanol. In addition, the conversion of ethyl acetate in the hydrogenolysis reactor 140 may be greater than 70%, e.g., greater than 85% or greater than 90%. This also allows third column to operate under less stringent conditions, e.g., with a lower reflux ratio. In addition, when an appreciable amount of alcohols having at least 4 carbons, such as n-butanol and/or 2-butanol, are produced through side reactions in the hydrogenolysis reactor 140, it is preferred not to return these higher alcohols to the hydrogenation step as the higher alcohols may react with acetic acid leading to a buildup of higher acetates in the process.

As shown in FIG. 6, preferably none of the second residue in line 152 is returned to hydrogenation zone 101. In addition, because the second distillate may comprise ethanol and ethyl acetate, it may not be necessary to add first distillate 132 thereto. Thus, first distillate 132 may be returned to decanter 120 as shown in FIG. 7.

3. Finishing Column

Figure 8A:
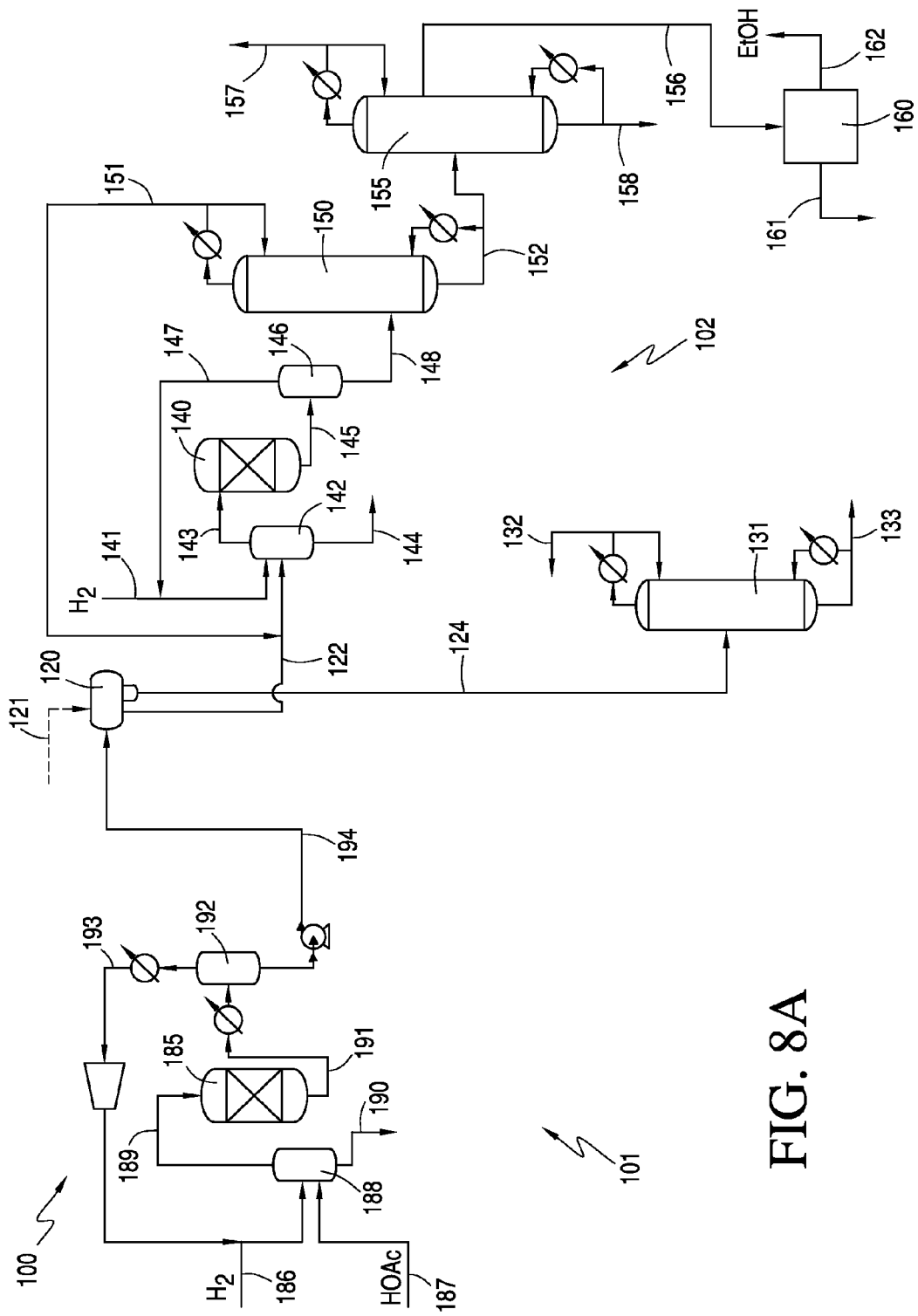
FIG. 8A is a schematic diagram of ethanol production process having a water separator for the ethanol product in the hydrogenolysis zone in accordance with one embodiment of the present invention.

In some embodiments, it may be necessary to further treat the second residue to remove additional heavy compounds such as higher alcohols and any light components from the ethanol. As shown in FIGS. 7A, 7B, and 8A, there is provided a finishing column 155, also referred to as a "fourth column." Second residue in line 152 is fed to a lower portion of fourth column 155. Fourth column 155 produces an ethanol sidestream in line 156, a third distillate in line 157 and a third residue in line 158. Preferably ethanol sidestream 156 is the largest stream withdrawn from fourth column 155 and is withdrawn at a point above the feed point of the second residue in line 152. In one embodiment the relative flow ratios of sidestream to residue is greater than 50:1, e.g., greater than 100:1 or greater than 150:1.

Ethanol sidestream 156 preferably comprises at least 90% ethanol, e.g., at least 92% ethanol and a least 95% ethanol. Depending on the amount of water fed to hydrogenolysis reactor 140, the water concentration in ethanol sidestream 156 may be less than 10 wt. %, e.g., less than 5 wt. % or less than 1 wt. %. In addition, the amount of other impurities, in particular diethyl acetal and 2-butanol, are preferably less than 0.05 wt. %, e.g., less than 0.03 wt. % or less than 0.01 wt. %. The third distillate in line 157 preferably comprises a weight majority of the diethyl acetal fed to fourth column 155. In addition, other light components, such as acetaldehyde and/or ethyl acetate may also concentrate in the third distillate. The third residue in line 158 preferably comprises a weight majority of the 2-butanol fed to fourth column 155. Heavier alcohols may also concentrate in the third residue in line 158.

Fourth column 155 may be a tray column or packed column. In one embodiment, Fourth column 155 is a tray column having from 10 to 100 trays, e.g., from 20 to 80 trays or from 30 to 70 trays. Fourth column 155 operates at a pressure ranging from 1 kPa to 510 kPa, e.g., from 10 kPa to 450 kPa or from 50 kPa to 350 kPa. Although the temperature of fourth column 155 may vary, the temperature of the residue exiting in line 158 preferably is from 70° C. to 105° C., e.g., from 70° C. to 100° C. or from 75° C. to 95° C. The temperature of the third distillate exiting in line 157 preferably is from 50° C. to 90° C., e.g., from 55° C. to 85° C. or from 65° C. to 80° C. Ethanol sidestream 156 is preferably withdrawn at the boiling point of ethanol, about 78° C. at atmospheric pressure. As shown in FIGS. 7A and 7B, a portion of the second distillate in line 151 is returned to hydrogenolysis zone 102.

In some embodiments, a portion of the third residue, sidestream or third distillate may be dehydrated to form aliphatic alkenes. In one embodiment, the 2-butanol in the third residue may be dehydrated to 2-butene. In another embodiment, the 2-butanol in the third residue stream may be recovered in a separate system.

In one embodiment, instead of purging the third distillate in line 157 or the third residue in line 158, a portion thereof may be fed to vaporizer 188. Heavy ends compounds may be removed in the blowdown stream 190.

The ethanol product may contain small concentrations of water. For some ethanol applications, in particular for fuel applications, it may be desirable to further reduce the water concentration. As shown in FIG. 8A, a portion of fourth column ethanol sidestream 156 is fed to a water separation unit 160. Water separation unit 160 may include an adsorption unit, one or more membranes, molecular sieves, extractive distillation units, or a combination thereof. Ethanol sidestream 156 may be withdrawn as a vapor or liquid stream, but it may be more suitable to use a vapor stream. Suitable adsorption units include pressure swing adsorption (PSA) units and thermal swing adsorption (TSA) units. In FIG. 8A, a PSA unit 160 may be employed to remove water from the sidestream 156. PSA unit 160 is operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. The water stream 161 may be purged and/or directed to recovery column 131. The resulting dried ethanol product stream 162 preferably has a water concentration that is less than 1 wt. %, e.g., less than 0.5 wt. % or less than 0.1 wt. %. The ethanol may be separated in line 159 prior to PSA unit 160 to increase the capacity of the water separation unit. This allows an impure ethanol recycle, if needed, and does not require additional capital to purify the ethanol prior to recycling.

Figure 8B:
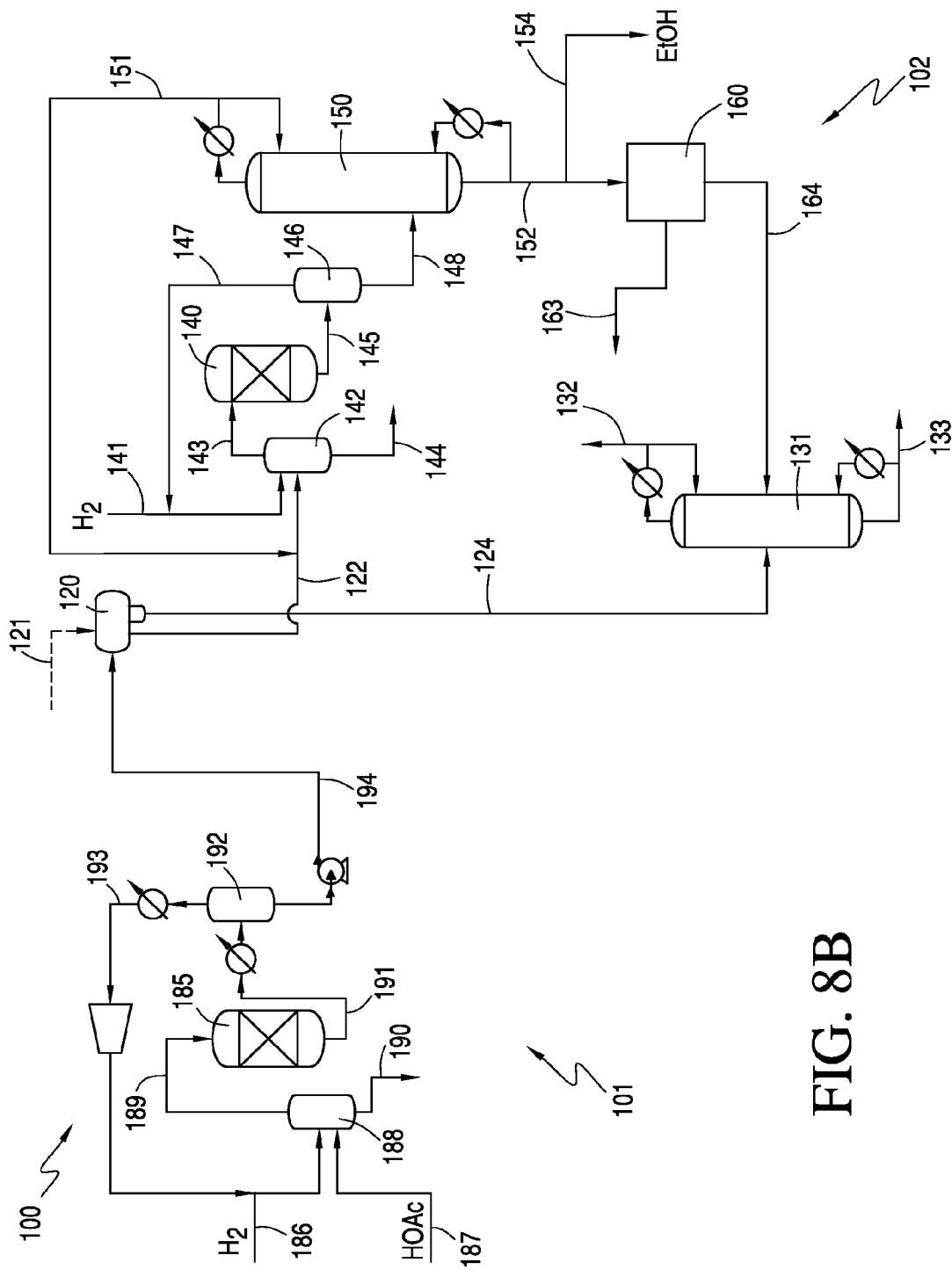
FIG. 8B is a schematic diagram showing a water separator for an ethanol return stream in accordance with one embodiment of the present invention.

In FIG. 8B, a water separation unit 160 may remove the water from a portion of the second residue in line 152 comprising ethanol. Depending on the ethanol application, the water concentration in second residue in line 152 may be sufficiently low and an ethanol product may be recovered in line 154. Water separation unit 160 removes a majority of the water in the second residue in line 152 to produce a dry ethanol return stream 163 and a water stream 164. Dry ethanol return stream 163 has a water concentration that is less than 1 wt. %, e.g., less than 0.5 wt. % or less than 0.1 wt. %. Water stream 164 may be purged or fed to recovery column 131 to remove any organics, including ethanol, prior to purging. The distillate in line 132 may be combined with dry ethanol return stream 163 or fed to decanter 120.

In some embodiments the desired ethanol product is an anhydrous ethanol that is suitable for uses as a fuel or as a blend for other fuels, such as gasoline. Water separation unit 160 as described herein may be suitable for producing anhydrous ethanol.

Figure 9A:
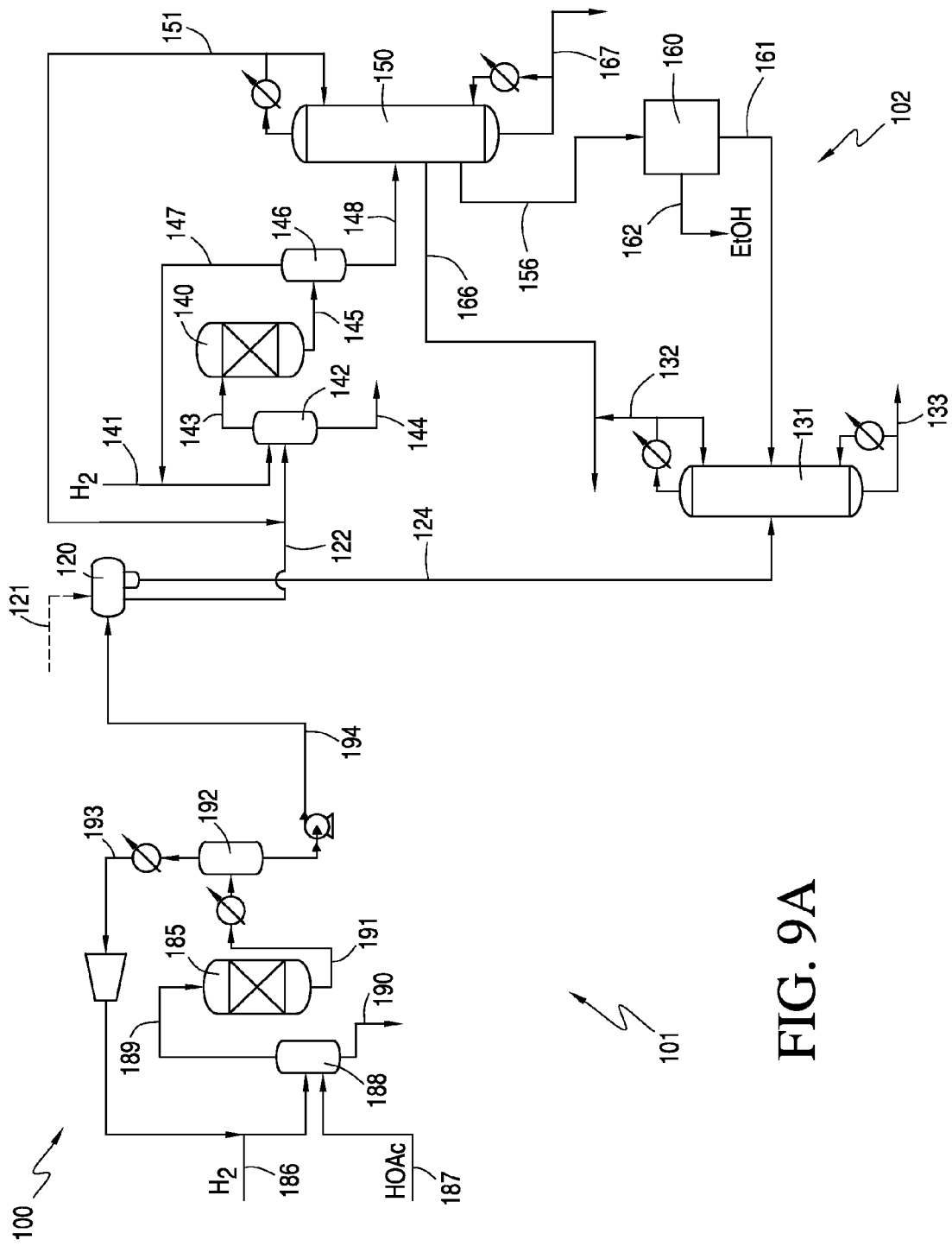
FIG. 9A is a schematic diagram showing a water separator for producing anhydrous ethanol in accordance with one embodiment of the present invention.
Figure 9B:
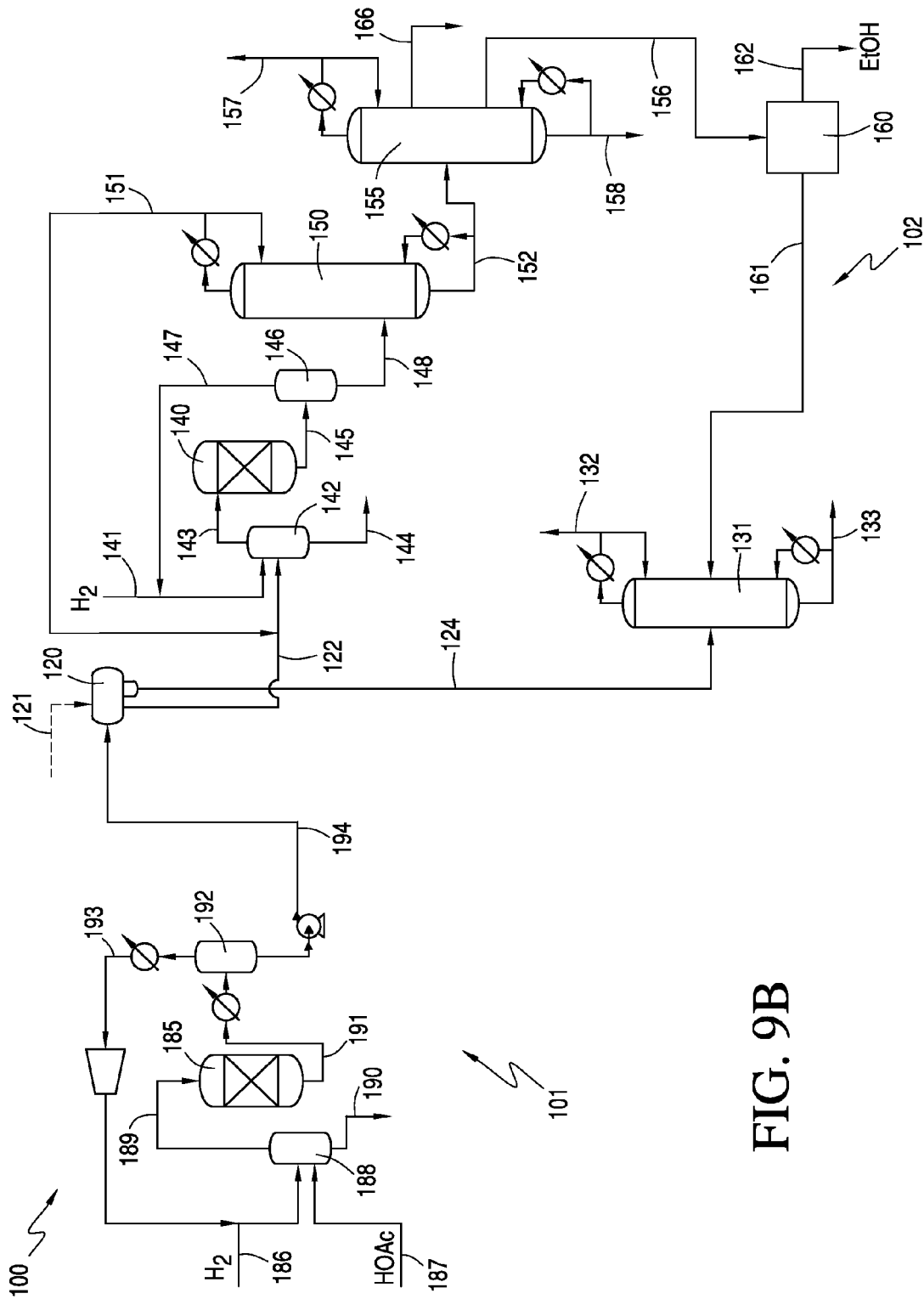
FIG. 9B is a schematic diagram of ethanol production having separate liquid ethanol return stream and water separator for the ethanol product in the hydrogenolysis zone in accordance with one embodiment of the present invention.

FIGS. 9A and 9B are schematics in which liquid ethanol stream 166 and ethanol sidestream 156 are withdrawn. Preferably ethanol sidestream 156 is a vapor sidestream that may be directed fed to a pressure swing adsorption unit or membrane to remove water. In one embodiment, ethanol sidestream 156 may be taken near the reboiler of the respective column to allow a single stage flashing to remove heavy components that may be present. Liquid ethanol stream 166 may comprise ethanol, ethyl acetate, water and/or mixtures thereof. Liquid ethanol stream 166 may be withdrawn at a point higher in the respective column, but preferably below the feed location to the column. In FIG. 9A, liquid ethanol stream 166 and ethanol sidestream 156 are withdrawn from second distillation column 150. Advantageously ethanol sidestream 156 is withdrawn such that heavy components, which may be unsuitable for fuel applications, are removed in second distillation column in the residue. The residue in line 167 of second distillate column 150 contains heavy components, e.g. acetic acid, acetates, and heavy alcohols, such as n-butanol and 2-butanol. The residue in line 167 may be purged. In some embodiments, residue in line 167 may comprise ethanol and/or acetic acid and the residue in line 167 to vaporizer 188. The heavier components are then removed in the blowdown stream 190. In FIG. 9B, liquid ethanol stream 166 and ethanol sidestream 156 are withdrawn from third distillation column 155. Similar to the residue of second distillation column 150, the residue in line 158 from third distillation column 155 may also be purged or returned to vaporizer 192.

Ethanol sidestream 156 is preferably a vapor stream that is directed to water separation unit 160 to yield a water stream 161 and dried ethanol product stream 162. Water separation unit 160 may include an adsorption unit, one or more membranes, molecular sieves, extractive distillation units, or a combination thereof. More preferably water separation unit 160 may be a pressure swing adsorption unit. The vapor ethanol sidestream 156 may comprise less than 10 wt. % water, e.g., less than 8 wt. % or less than 5 wt. %. Water separation unit 160 removes at least 85% of the water in ethanol sidestream 156, e.g. at least 90% or at least 95%. The resulting dried ethanol product stream 162 may have a water concentration that is less than 2 wt. %, e.g. less than 1 wt. %, or less than 0.5 wt. %. Dried ethanol product stream 162 may be used as a fuel-grade ethanol and may be blended with gasoline.

A wet ethanol stream 161 is also obtained from water separation unit 160 directed to recovery column 131 to recover any ethanol.

The columns shown in the figures may comprise any distillation column capable of performing the desired separation and/or purification. For example, unless described otherwise, the columns may be tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

For purposes of the present invention, exemplary ethanol compositional ranges are provided below in Table 6. Depending on the application of the ethanol, one or more of the other organic impurities listed in Table 6 may be present.

TABLE 6

FINISHED ETHANOL COMPOSITIONS

| Component | Conc. (wt. %) | Conc. (wt. %) | Conc. (wt. %) |
| --- | --- | --- | --- |
| Ethanol | 75 to 99.9 | 88 to 99.5 | 90 to 96 |
| Water | <12 | 0.01 to 7.5 | 0.5 to 5 |
| Acetic Acid | <0.1 | <0.01 | <0.005 |
| Ethyl Acetate | <0.1 | <0.01 | <0.005 |
| Isopropanol | <0.5 | <0.1 | <0.05 |
| Diethyl Acetal | <0.5 | <0.1 | <0.05 |
| n-butanol | <0.5 | <0.1 | <0.05 |
| 2-butanol | <2 | <0.5 | <0.1 |
| Acetone | <0.5 | <0.1 | <0.05 |

In one embodiment, the recovered ethanol may have a composition that is from 92 wt. % to 97 wt. % ethanol, 3 wt. % to 8 wt. % water, 0.01 wt. % to 0.2 wt. % 2-butanol, and 0.02 wt. % to 0.08 wt. % isopropanol. The amount of 2-butanol may be greater than isopropanol. Preferably, other than 2-butanol and isopropanol, the recovered ethanol comprises less than 1 wt. % of one or more organic impurities selected from the group consisting of acetaldehyde, acetic acid, diethyl acetal, and ethyl acetate. The 2-butanol concentration in the ethanol sidestream may be reduced to an amount that is less than 0.01 wt. % when using a finishing column.

III. Uses of Ethanol

Ethanol produced by the embodiments of the present invention may be used in a variety of applications including fuels, solvents, chemical feedstocks, pharmaceutical products, cleansers, sanitizers, hydrogenolysis transport or consumption. In fuel applications, ethanol may be blended with gasoline for motor vehicles such as automobiles, boats and small piston engine aircraft. In non-fuel applications, ethanol may be used as a solvent for toiletry and cosmetic preparations, detergents, disinfectants, coatings, inks, and pharmaceuticals. Ethanol may also be used as a processing solvent in manufacturing processes for medicinal products, food preparations, dyes, photochemicals and latex processing.

Ethanol may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In another application, ethanol may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, examples are provided below. It should be understood that these examples are for illustrative purposes only and are not to be construed as limiting the invention in any manner.

EXAMPLES

Example 1

Hydrogenolysis Catalyst

The hydrogenolysis was carried out in a vapor-phase, heterogeneously catalyzed, continuously stirred tank (Berty type) reactor. The catalyst was T-2130™ (Süd Chemie), which has the following composition: CuO (26%), ZnO (53%). The hydrogenolysis catalyst was reduced at an operating pressure of 690 kPa with an initial temperature of 120° C. that was increased to 170° C. while introducing a low flow rate of hydrogen gas into a constant inert gas feed stream to the reactor to achieve a hydrogen concentration of 0.5-1.0% $H_2$. The $H_2$ concentration was slowly increased stepwise to 2.2%, 3.5%, 4.0%, 5.0% and 6.0% and then was held at a constant reactor temperature of 215° C.

A mixture of $H_2$ (93.6 mol %), $N_2$ (2.5 mol %), and ethyl acetate (3.9 mol %) was passed over 52.9 g T-2130™ catalyst at 260° C., with a pressure of 4140 kPa and GHSV of 6000 $hr^{-1}$. The LHSV was 1.0 $hr^{-1}$. The observed conversion of ethyl acetate was 86.4% with a selectivity to ethanol of 92.0%. The observed productivity of ethanol (g EtOH/kg catalyst/hr) was 510 g EtOH/kg catalyst/hr.

Example 2

Hydrogenolysis Catalyst

Operating under the same conditions as Example 1, a mixture of $H_2$ (84.5 mol %), $N_2$ (9.0 mol %), and ethyl acetate (6.5 mol %) was passed over 52.9 g T-2130™ at 240° C., with a pressure of 4140 kPa, GHSV of 1700 $hr^{-1}$, and LHSV at 0.47 $hr^{-1}$. The observed conversion of ethyl acetate was 87.8% and the selectivity to ethanol was 96.4%. The observed productivity of ethanol (g EtOH/kg catalyst/hr) was 290 g EtOH/kg catalyst/hr.

Example 3

Hydrogenolysis Catalyst

MegaMax700™ (Süd Chemie), which has the following composition: CuO (61%), ZnO (28%), $Al_2O_3$ (10%) was used in place of the T-2130™ catalyst in Example 1. The operating conditions were similar as to Example 1. A mixture of $H_2$ (92.0 mol %), $N_2$ (2.7 mol %), and ethyl acetate (5.3 mol %) was passed over 38.72 g MegaMax700™ at 250° C. at an operating pressure of 2410 kPa, a GHSV of 5460 $hr^{-1}$, and a LHSV of 1.3 $hr^{-1}$. The observed conversion of ethyl acetate was 80.1% and the selectivity to ethanol was 85.1%. The observed productivity of ethanol (g EtOH/kg catalyst/hr) was 848 g EtOH/kg catalyst/hr.

Example 4

Hydrogenolysis Catalyst

Operating under the same conditions as Example 3, a mixture of $H_2$ (90.4 mol %), $N_2$ (2.4 mol %), and ethyl acetate (7.2 mol %) was passed over 38.72 g MegaMax700™ at 250° C. at an operating a pressure of 5520 kPa, a GHSV of 6333 $hr^{-1}$, and a LHSV of 2.0 $hr^{-1}$. The observed conversion of ethyl acetate was 81.9% and the selectivity to ethanol was 89.0%. The observed productivity of ethanol (g EtOH/kg catalyst/hr) was 1470 g EtOH/kg catalyst/hr.

Example 5

Heavy Impurities in Hydrogenolysis

MegaMax700™ (38.72 g) was used to catalyze hydrogenolysis reactions with mixtures of $H_2$ and ethyl acetate under operating conditions with reaction temperatures in a range from 250° C. to 275° C., pressure ranges from 350 to 800 psig and GHSV values ranging from 3693 to 6333 $hr^{-1}$. The average conversion of ethyl acetate was 83.7% and the average selectivity to ethanol was 84.2%. Higher alcohols ($C_3$-$C_4$) detected in condensed hydrogenolysis reactor product samples included isopropanol, 2-butanol, and 1-butanol as shown in Table 7.

TABLE 7

|  | 22 | 23 | 24 | 25 | 26 | 27 |
| --- | --- | --- | --- | --- | --- | --- |
| Reactor Pressure (psig) | 367 | 356 | 357 | 354 | 816 | 803 |
| Reactor Temperature (° C.) | 250 | 250 | 275 | 275 | 250 | 252 |
| GHSV (1/hr) | 3693 | 5455 | 3684 | 5452 | 5100 | 6333 |
| Ethyl Acetate LHSV (1/hr) | 0.9 | 1.3 | 0.8 | 1.2 | 1.6 | 2.0 |
| Conversion of Ethyl Acetate (%) | 85.7 | 80.1 | 86.9 | 82.9 | 85.0 | 81.9 |
| Selectivity to Ethanol (%) | 80.3 | 85.1 | 78.1 | 83.7 | 89.0 | 89.0 |
| iso-propanol (wt %) | 0.072 | 0.049 | 0.244 | 0.186 | 0.037 | 0.019 |
| 2-butanol (wt %) | 0.561 | 0.484 | 1.83 | 1.50 | 0.403 | 0.332 |
| 1-butanol (wt %) | 0.119 | 0.130 | 0.516 | 0.415 | 0.096 | 0.066 |

Example 6

Reduction of Heavy Impurities

A mix of ethyl acetate (87.6 wt %), ethanol (8.55 wt %), and water (3.8 wt %) was fed to a hydrogenolysis reactor. The liquid was vaporized to form a gaseous stream of $H_2$ (89.2 mol %), $N_2$ (4.0 mol %), EtOAc (5.0 mol %), EtOH (0.8 mol %), and water (0.9 mol %). The gas stream reacted over Mega-Max700™ at 275° C., with a pressure of 2514 kPa and GHSV of 5464 $hr^{-1}$ and the LHSV was 1.3 $hr^{-1}$. The observed conversion of ethyl acetate was 80.4% and the selectivity to ethanol was 94.2%. The observed productivity of ethanol (g EtOH/kg catalyst/hr) was 878.9 g EtOH/kg catalyst/hr. The same reaction was performed with pure ethyl acetate as the feedstock, and the concentration of impurities are compared in Table 8. Reduction (%)=(wt % impurity with pure EtOAc−wt % impurity with mix feed)/(wt % impurity with pure EtOAc)*100

TABLE 8

| Impurity | Wt % (pure EtOAc) | Wt % (EtOAc—EtOH-water mix) | Reduction (%) |
|---|---|---|---|
| 2-Butanol | 1.499 | 0.778 | 48.1 |
| 1-Butanol | 0.415 | 0.124 | 70.1 |
| Heavies | 0.836 | 0.278 | 66.8 |
| average | — | — | 61.7 |
| EtOH selectivity | 81.8% | 91.8% | |

Example 7

Ethanol Product

Table 9 compares the ethanol product obtained from hydrogenolysis compared to fermentation, ethylene dehydrated, and acetic acid hydrogenation. Comparative A is a fermentation process that uses sugarcane and Comparative B is a fermentation process that uses molasses. Comparative C is a Fischer-Tropsch process. Comparative D is an acetic acid hydrogenation process. The ethanol product is shown as recovered using a finishing column and without a finishing column. The finishing column removes a significant amount of n-butanol and 2-butanol.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A method of producing ethanol comprising:
   hydrogenating acetic acid in a first reactor in the presence of a first catalyst to form a hydrogenation product comprising ethyl acetate, water, and acetic acid;
   introducing the hydrogenation product to a decanter to be condensed and biphasically separated into an organic phase and aqueous phase, and wherein the organic phase is the ester feed stream; and
   reducing the ester feed stream in a second reactor in the presence of a second catalyst to form ethanol;
   wherein at least 70% acetic acid is converted and further wherein less than 45% of the acetic acid is converted to ethanol.

2. The method of claim 1, wherein the ester feed stream is recovered in the absence of an esterification process.

3. The method of claim 1, wherein none of the ethanol formed by reducing the ester feed stream is recycled to the first reactor.

4. The method of claim 1, wherein the hydrogenation product comprises from 20 to 95 wt. % ethyl acetate, 5 to 40 wt. % water and 0.01 to 30 wt. % acetic acid.

5. The method of claim 1, wherein the hydrogenation product further comprises from 0.1 to 30 wt. % ethanol.

6. The method of claim 1, wherein the organic phase is further separated in an extractive column using at least one extractive agent and obtaining an extractant stream and an ethyl acetate rich extractant stream from the extractive column, and wherein the ethyl acetate rich extractant stream is the ester feed stream fed to the second reactor.

TABLE 9

| Component | Without finishing | With finishing | Fermentation A | B | C | D |
|---|---|---|---|---|---|---|
| Ethanol | 95.2 wt. % | 95.4 wt. % | 93.4 wt. % | 93.4 wt. % | 93.1 wt. % | 92.7 wt. % |
| Water | 4.5 wt. % | 4.5 wt. % | 6.6 wt. % | 6.5 wt. % | 6.9 wt. % | 7.4 wt. % |
| Acetic Acid | 47 wppm | 0 | 11 wppm | 10 wppm | 8 wppm | 14 wppm |
| Ethyl Acetate | 4 wppm | 2 wppm | 51 wppm | — | — | 70 wppm |
| Isopropanol | 394 wppm | 357 wppm | 2 wppm | 17 wppm | 10 wppm | 110 wppm |
| n-propanol | — | — | 238 wppm | 109 wppm | 121 wppm | 160 wppm |
| n-butanol | 413 wppm | 1 wppm | — | — | — | — |
| 2-butanol | 1548 wppm | 94 wppm | — | — | — | — |
| $C_4$ alcohols | 1961 wppm | 95 wppm | 35 wppm | 20 wppm | 17 wppm | 21 wppm |
| $C_5$ alcohols | — | — | 12 wppm | 11 wppm | 5 wppm | 0 |
| $C_{2+}$ alcohols | 2355 wppm | 452 wppm | 288 wppm | 156 wppm | 261 wppm | 291 wppm |
| Acetaldehyde | 0 | 0 | 29 wppm | 18 wppm | 4 wppm | 5 wppm |
| Methanol | — | — | 51 wppm | 42 wppm | 46 wppm | not detectable |

7. The method of claim 1, wherein the hydrogenation product is fed to directly to a decanter without any intervening separation.

8. The method of claim 1, wherein the ester feed stream comprises less than 5 wt. % ethanol and less than 5 wt. % water.

9. The method of claim 1, wherein the second catalyst comprises a catalyst selected from the group consisting of a copper-based catalyst and a Group VIII-based catalyst.

10. The method of claim 1, wherein the molar ratio of hydrogen to ethyl acetate fed to the second reactor is from 2:1 to 100:1.

11. The method of claim 1, wherein the second reactor is operated at a temperature from 125° C. to 350° C. and a pressure of 700 to 8,500 kPa.

12. The method of claim 1, wherein the first catalyst has a selectivity to ethyl acetate that is greater than 50%.

13. The method of claim 1, wherein the first reactor is operated at a temperature from 125° C. to 350° C., a pressure of 10 kPa to 5000 kPa, and a hydrogen to acetic acid mole ratio of greater than 4:1.

14. The method of claim 1, further comprising converting a carbon source into methanol and converting the methanol into the acetic acid, wherein the carbon source is selected from the group consisting of natural gas, petroleum, biomass, and coal.

15. The method of claim 1, further comprising converting a carbon source into syngas, converting at least a portion of the syngas into methanol, and converting the methanol into the acetic acid, wherein the carbon source is selected from the group consisting of natural gas, petroleum, biomass, and coal.

16. The method of claim 1, further comprising converting a carbon source into syngas, separating at least a portion of the syngas into a hydrogen stream and carbon monoxide stream, and reacting at least a portion of the carbon monoxide stream with methanol to form the acetic acid; wherein the carbon source is selected from the group consisting of natural gas, petroleum, biomass, and coal.

17. The method of claim 1, further comprising converting a carbon source into syngas, separating a portion of the syngas into a hydrogen stream and carbon monoxide stream, converting at least some of the syngas into methanol, and reacting a portion of the carbon monoxide stream with a portion of the methanol to form the acetic acid; wherein the at least a portion of the ester feed stream is reduced with at least a portion of the hydrogen stream.

18. A method of producing ethanol comprising:
hydrogenating acetic acid in a first reactor in the presence of a first catalyst to form a hydrogenation product comprising ethyl acetate, water, and acetic acid;
biphasically separating at least a portion of the hydrogenation product in a decanter into an organic phase comprising ethyl acetate and an aqueous phase comprising ethanol and water; and
reacting at least a portion of the organic phase with hydrogen in a second reactor to produce ethanol;
wherein at least 70% acetic acid is converted and further wherein less than 45% of the acetic acid is converted to ethanol.

19. A method of producing ethanol comprising:
hydrogenating acetic acid in a first reactor in the presence of a first catalyst to form a hydrogenation product comprising ethyl acetate, water, and acetic acid;
biphasically separating at least a portion of the hydrogenation product in a decanter into an organic phase comprising ethyl acetate and an aqueous phase comprising ethanol and water;
separating at least a portion of the aqueous phase in a first distillation column to yield a first distillate comprising ethanol and ethyl acetate, and a first residue comprising water; and
reacting at least a portion of the organic phase and at least portion of the first distillate with hydrogen in a second reactor to produce ethanol;
wherein at least 70% acetic acid is converted and further wherein less than 45% of the acetic acid is converted to ethanol.

20. The process of claim 19, wherein the hydrogenation product is fed directly to the decanter.

\* \* \* \* \*